US007884066B2

(12) United States Patent
Ting

(10) Patent No.: US 7,884,066 B2
(45) Date of Patent: Feb. 8, 2011

(54) NELL-1 ENHANCED BONE MINERALIZATION

(75) Inventor: Kang Ting, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 152 days.

(21) Appl. No.: 11/713,366

(22) Filed: Mar. 1, 2007

(65) Prior Publication Data

US 2008/0274186 A1  Nov. 6, 2008

Related U.S. Application Data

(63) Continuation-in-part of application No. 10/544,553, filed as application No. PCT/US2004/003808 on Feb. 9, 2004, now Pat. No. 7,544,486, and a continuation-in-part of application No. 11/392,294, filed on Mar. 28, 2006, which is a continuation of application No. 09/412,297, filed on Oct. 5, 1999, now Pat. No. 7,052,856.

(51) Int. Cl.
*A61K 38/00* (2006.01)
*A61K 38/16* (2006.01)
*A61K 38/17* (2006.01)
*A61K 38/18* (2006.01)

(52) U.S. Cl. .................. 514/1.1; 514/16.7; 514/16.8; 514/16.9; 514/17.1

(58) Field of Classification Search ............ None
See application file for complete search history.

(56) References Cited

U.S. PATENT DOCUMENTS

| | | | |
|---|---|---|---|
| 4,394,370 | A | 7/1983 | Jefferies |
| 4,409,332 | A | 10/1983 | Jefferies et al. |
| 5,385,887 | A | 1/1995 | Yim et al. |
| 5,486,359 | A | 1/1996 | Caplan et al. |
| 5,674,725 | A | 10/1997 | Beertsen et al. |
| 5,674,844 | A | 10/1997 | Kuberasampath et al. |
| 5,763,416 | A | 6/1998 | Bonadio et al. |
| 5,854,207 | A | 12/1998 | Lee et al. |
| 5,916,870 | A | 6/1999 | Lee et al. |
| 5,942,496 | A | 8/1999 | Bonadio et al. |
| 5,948,428 | A | 9/1999 | Lee et al. |
| 6,077,987 | A | 6/2000 | Breitbart et al. |
| 6,083,690 | A | 7/2000 | Harris et al. |
| 6,200,606 | B1 | 3/2001 | Peterson et al. |
| 6,352,972 | B1 | 3/2002 | Nimni et al. |
| 6,413,998 | B1 | 7/2002 | Petrie et al. |
| 6,462,019 | B1 | 10/2002 | Mundy et al. |
| 2003/0143688 | A1 | 7/2003 | Fujiwara et al. |

FOREIGN PATENT DOCUMENTS

| | | |
|---|---|---|
| WO | WO 01/24821 | 4/2001 |
| WO | WO 2004/024893 | 3/2004 |

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Bork et al., 1996, Trends in Genetics 12:425-427.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Liu et al., "Simultaneous Detection of Multiple Bone-Related mRNAs and Protein Expression during Osteoblast Differentiation: Polymerase Chain Reaction and Immunocytochemical Studies at the Single Cell Level", Developmental Biology, vol. 166, pp. 220-234 (1994).
Zhang et al., "NELL-1 Overexpression Transgenic Mice Simulate Human Craniosynostosis", Surgical Forum, vol. 52, pp. 576-578 (2001).
International Search Report for PCT/US04/03808 filed Feb. 9, 2004, mailed Sep. 16, 2006, 9 pgs.
Beck et al. "Rapid Publication TGF-$\beta_1$ Induces Bone Closure of Skull Defects." J. of *Bone Miner. Res*. vol. 6, No. 11:1257-1265 (1991).
Bellows et al. "Determination of Numbers of Osteoprogenitors Present in Isolated Fetal Rat Calvaria Cells in Vitro." Dev. Biol. 133, pp. 8-13 (1989).
Burger et al., "Osteoblast and Osteoclast Precursors in Primary Cultures of Calvarial Bone Cells." Anat. Rec. Jan. 1986; 214(1): 32-40. Abstract only.
Chen et al. "Structure, Chromosomal Localization, and Expression Pattern of the Murine *Magp* Gene," J. Biol Chem. vol. 268, No. 36: 27381-27389 (1998).
Crawford et al. "Thrombospondin-1 is a Major Activator of TGF-$\beta_1$ in Vivo." Cell, vol. 93:1159-1170 (1998).
Francois and Bier "*Xenopus* chordin and *Drosophila* short gastrulation Genes Encode Homologous Proteins Functioning in Dorsal-Ventral Axis Formation" Cell, vol. 80:19-20 (1995).
Gelbart, "Databases in Genomic Research" Science, vol. 282, Oct. 23, 1998.
Hoshi, K. et al., "Fibroblasts of Spinal Ligaments Pathologically Differentiate into Chondrocytes Induced by Recombinant Human Bone Morphogenetic Protein-2: Morphological Examinations for Ossification and Spinal Ligaments" Bone vol. 21, No. 2: 155-162 (1997).
Kim et al. "NELL-1 Enhances Mineralization in Fetal Calvarial Osteoblastic Cells." Plastic Surgery, 599-601 (1999) .
Kuroda and Tanizawa "Involvement of Epidermal Growth Factor-like Domain of NELL Proteins in the Novel Protein-Protein Interaction with Protein Kinase C[1]" Biochem Biophys Res. Commun. 265: 752-757 (1999).

(Continued)

*Primary Examiner*—Elizabeth C. Kemmerer
(74) *Attorney, Agent, or Firm*—Squire Sanders & Dempsey, L.L.P.

(57) ABSTRACT

Provided herein are methods for enhancing bone mineralization for bone repair or regeneration and compositions and grafts therefor. Methods for screening agents that enhance or modulate NELL-1 gene expression or NELL-1 protein production in a cell are also provided.

12 Claims, 8 Drawing Sheets

OTHER PUBLICATIONS

Kuroda et al. "Biochemical Characterization and Expression Analysis of Neural Thrombospondin-1-like Proteins NELL1 and NELL2" Biochem Biophys Res Comm. 265: 79-86 (1999).

Luce and Burrows "The neuronal EGF-related genes NELL1 and NELL2 are expressed in hemopoietic cells and developmentally regulated in the B lineage" *Gene* 231:121-126 (1999).

Opperman, et al., "TGF-β1, TGF-β2, and TGF-β3 Exhbit Distinct Patterns of Expression During Cranial Suture Formation and Obliteration In Vivo and In Vitro" J. of Bone and Mineral Research, vol. 12, No. 3: 301-310 (1997).

Piccolo et al. "Dorsoventral Patterning in *Xenopus*: Inhibition of Ventral Signals by Direct Binding of Chordin to BMP-4" Cell, vol. 86: 589-598 (1996).

Siris et al., "Design of NORA, the National Osteoporosis Risk Assessment program: A Longitudinal US Registry of Postmenopausal Women" Osteoporos Int. Suppl. 1: 62-69 (1998).

Takagi et al. "The reaction of the dura to bone morphogenetic protein (BMP) in repair of skull defects" Ann Surg. vol. 196, No. 1: 100-109. Abstract only (1982).

Takami et al. "$CA^{2+}$-ATPase Inhibitors and $Ca^{2+}$-Ionophore Induce Osteoclast-like Cell Formation in the Cocultures of Mouse Bone Marrow Cells and Calvarial Cells" Biochemical and Biophysical Research Comm, vol. 237: 111-115 1997.

Tieu A. et al. "Identification of Human NEL-2 Associated with Premature Suture Fusion." J Dent Res. 77(A):635, Abstract only (1998).

Ting et al. "Human NELL1 Expressed in Unilateral Coronal Synostosis" J. of Bone and Mineral Res. vol. 14: 80-89 (1999).

Ting et al. "NELL-1 Enhances Mineralization in Fetal Calvarial Osteoblastic Cells." J. Dent. Res. 79:625 (2000).

Ting et al. "NEL-2 Expressed in Unilateral Prematurely Fusing and Fused Coronal Sutures." J Dent Res. 77(B):2224 (1998) Abstract only.

Ting et al. "NEL-2 Gene is associated with bone formation in Craniosynostosis", Plastic Surgery, 602-603 (no date).

Toriumi et al. "Mandibular Reconstruction With a Recombinant Bone-Inducing Factor." Arch. Otolaryngol. Head Neck Surg. vol. 117: 1101-1112 (1991).

Watanabe, T.K. et al. "Cloning and Characterization of Two Novel Human cDNAs (NELL1 and NELL2) Encoding Proteins with Six EGF-like Repeats." Genomics, vol. 38, 273-276 (1996).

Wobus, "Potential of embryonic stem cells" Molecular Aspects of Medicine (2001), 22/3 (149-164) (Abstract only) 1 pg.

Yasko et al. "The Healing of Segmental Bone Defects, Induced by Recombinant Human Bone Morphogenetic Protein (rhBMP-2)." J. of Bone and Joint Surgery vol. 74A, No. 5: 659-670 (1992).

Zhang et al., "Graniosynostosis in transgenic mice overexpressing Nell-1" The J. of Clinical Investigation, vol. 110, No. 6 (2002).

International Search Report for PCT/US2008/054779, mailed Aug. 1, 2008, 11 pgs.

Aghaloo et al., "Nell-1-induced bone regeneration in calvarial defects", Am. J. Pathol., vol. 169, pp. 903-915 (2006).

Cowan et al., "Nell-1 induced bone formation within the distracted intermaxillary suture", Bone, vol. 38, pp. 48-58 (2006).

Lu et al., "The osteoinductive properties of Nell-1 in a rat spinal fusion model", The Spine J. vol. 7, No. 1, pp. 50-60 (2007).

\* cited by examiner

*Fig. 1A*
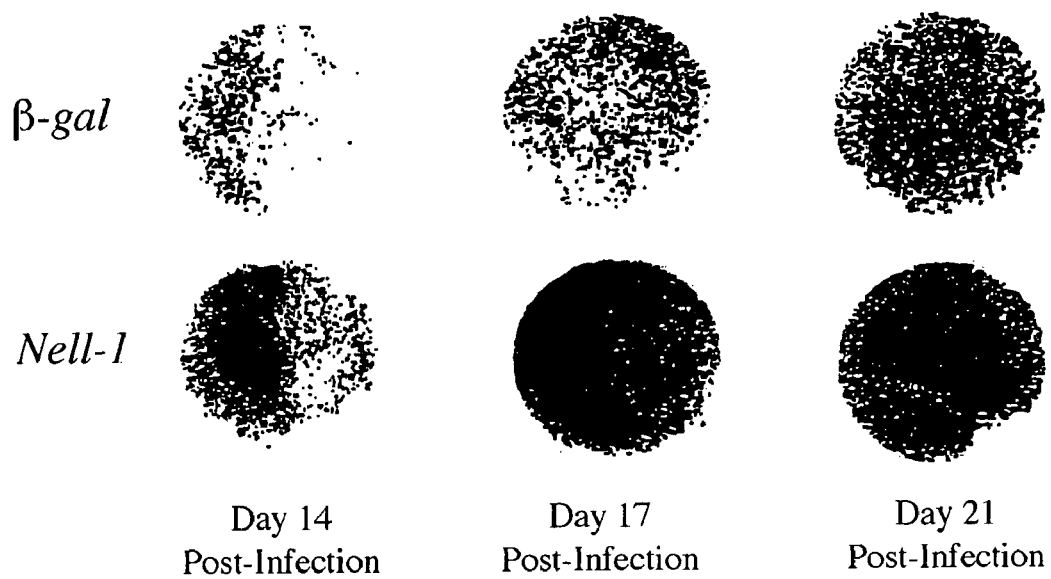
Day 14 Post-Infection    Day 17 Post-Infection    Day 21 Post-Infection
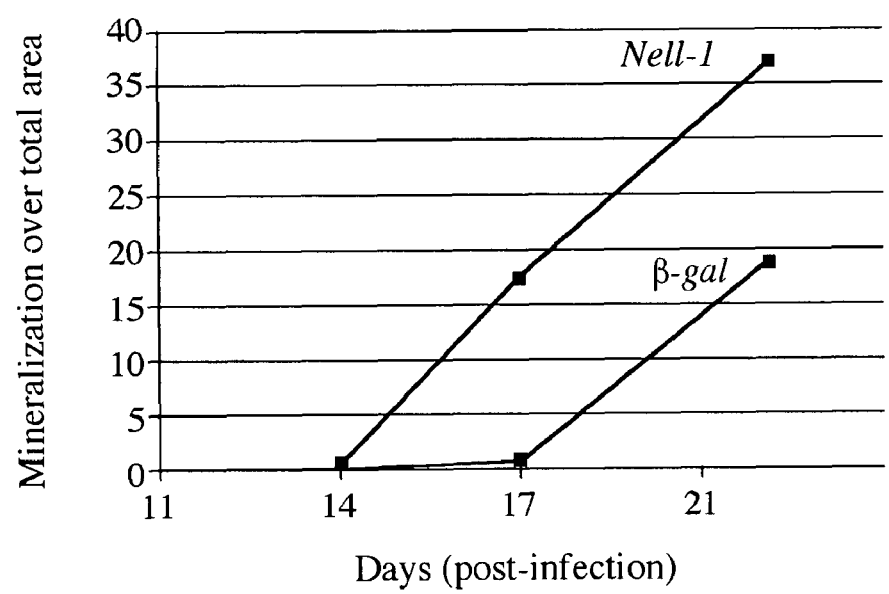
*Fig. 1B*

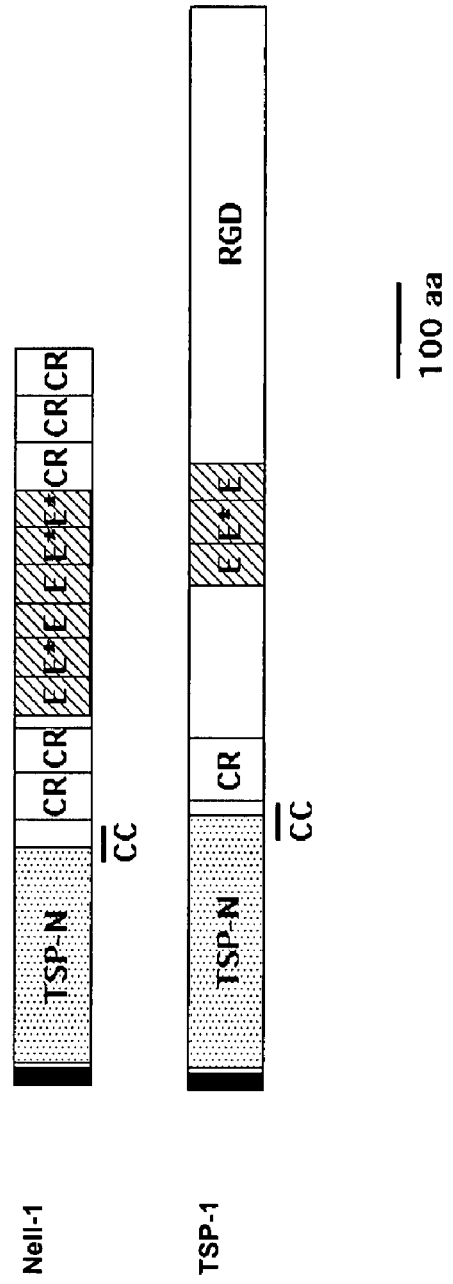
Figure 2. Schematic structures of rat Nell-1 protein and mouse TSP-1

Figure 3. Correlation of amino acid sequence with specific domains

```
Original Kuroda (1999) (Rat?)
NP_006148 / BAA11680 Human NELL-1

Signal Peptide                                   TSP-N (TSP-like)
Kuroda     1  MPMDVILVLW FCVCTARTVL GFGMDPDLQ L DLISELDLVN TTLGV HQVHG LHNASKAFLF
NP_006148     MPMDLILVVW FCVCTARTVV GFGMDPDLQM DIVTELDLVN TTLGVAQVSG MHNASKAFLF 61 QDVQREIHSA PHVSEKLIQL F RNKSEFTIL ATVQQKPSTS GVILSIRELE HSYFELESSG
              QDIEREIHAA PHVSEKLIQL FQNKSEFTIL ATVQQKPSTS GVILSIRELE HSYFELESSG 121 PREEIRYHYI HSGKPRTEA P PYRMADGQWH KV ALSVSASH LLLHIDCNRI YERVIDPP ET
          121 LRDEIRYHYI HNGKPRTEAL PYRMADGQWH KVALSVSASH LLLHVDCNRI YERVIDPPDT
              [ Orbigen] EAL PYRMADGQWH KVALC 181 NLPPGENLWL GQRNQKHG EF KGIIQDGKII FMPNG HITQC PNLNHTCPTC SDFLSLV QGI
              NLPPGINLWL GQRNQKHGLF KGIIQDGKII FMPNGYITQC PNLNHTCPTC SDFLSLVQGI
              (Coiled-coil within TSP-N)                                  CR-1 (vWF C domain)
          241 MDLQELLAKM TAKLAY AETR LEQLENCH CE KTCQVSGLIY RDQDSWVDGD HCRNCTCKSG
              MDLQELLAKM TAKLNYAETR LSQLENCHCE KTCQVSGLLY RDQDSWVDGD HCRNCTCKSG 301 AVECRRMSCP PLNCSPDSLP VHI SQQCCKV CRPKCIYGGK VLAEGQRILT K SCRECRGGV
              AVECRRMSCP PLNCSPDSLP VHIAGQCCKV CRPKCIYGGK VLAEGQRILT KSCRECRGGV
              [Abnova] CRRMSCP PLNCSPDSLP VHIAGQCCKV CRPKCIYGGK VLAEGQRILT KSCRECRGGV
                                                                          EGF-1 (EGF-like)
          361 LVKITEHCPP LNCS NRDHIL PENQCCRVC E GHNFCAEAPK CGENSECKNM NTK ATCECKN
              LVKITEMCPP LNCSEKDHIL PENQCCRVCR GHNFCAEGPK CGENSECKNM NTKATCECKS
              LVKITEMCPP LNCSEKDHIL PENQCCRVCR GHNFCAEGPK CGE
                             CR-2/Ca 2+-binding type EGF-like)                    //→
          421 GYISVQG SA YCEDIDECAA KMHYCHANTV CVNLPGLYRC DCVPGVIRVD DFSC TEHDDC
              GYISVQGDSA YCEDIDECAA KMHYCHANTV CVNLPGLYRC DCVPGVIRVD DFSCTEHDEC
                          EGF-3 (EGF-like)                EGF-4 (EGF-like)              //→
          481 GSGQHNCD N AICTNTVQGH SCTC IPGVVG NGTIC KAFCE EGCRYGGTCV APNKCVCPSG
              GSGQHNCDEN AICTNTVQGH SCTC HN SRCVNLP GWYHCERSG FHDDGTYSLS GESC IDIDEC
              FTGSHCEKDI DECSEGIIEC HNHSRCVNLP GWYHCERSG FHDDGTYSLS GESCIDIDEC
                     EGF-5/Ca (Ca 2+-binding type EGF-like)       CR-3 (vWF C domain)
          541 FTGSHCEKDI DEC EGIVEC HN SRCVNLP GWYHCERSG FHDDGTYSLS GESC IDIDEC
              ALRTHTCWND SACINLAGGF DCLCPSGPSC SGDCPHEGGL KHNGQVWTLK EDRCSVCSCK
              ALRTHTCWND SACINLAGGF DCLCPSGPSC SGDCPHEGGL KHNGQVWTLK EDRCSVCSCK
                   EGF-6/Ca (Ca 2+-binding type EGF-like )       CR-4 (vWF C domain)
          601 ALRTHTCWND S ACINLAGGF DCLCPSGPSC SGDCPHEGGL KHNGQV SQ KLYRSGDNWT HSCQQCRCLE
              DGKIFCRRTA CDCQNPSADL FCCPECDTRV TSQCLDQNGH KLYRSGDNWT HSCQQCRLE
                                                            CR-5 (vWF C domain)
          661 DGKIFCRRT A CDCQRPNVDL FCCPECDTRV TSQ CLEQ SGQ KLYRSGDNWT HSCQQCRCLE
              GEVDCWPLTC PNLSCEYTAI LEGECCPRCV SDPCLADNIT YDIRKTCLDS YGVSRLSGSV 721 GEADCWPLEC PSLSCEYTAM EEGECCPRCV SDPCLADNIA YDIRKTCLDS EGVSRLSGAV
              GEVDCWPLTC PNLSCEYTAI LEGECCPRCV SDPCLADNIT YDIRKTCLDS YGVSRLSGSV 781 WTM AGSPCTT CKCKNGRVCC SVD ECIENN
          781 WTMAGSPCTT CKCKNGRVCC SVDFECLQNN
```

Figures 4A-4D.

Sequence of 6-EGF like repeats

CAEAPKCGENSECKNWNTKATCECKNGYISVQGNSAYCEDIDECAAKMHYCH
ANTVCVNLPGLYRCDCVPGYIRVDDFSCTEHDDCGSGQHNCDKNAICTNTVQG
HSCTCQPGYVGNGTICKAFCEEGCRYGGTCVAPNKCVCPSGFTGSHCEKDID
ECAEGFVECHNYSRCVNLPGWYHCECRSGFHDDGTYSLSGESCIDIDECALRT
HTCWNDSACINLAGGFDCLCPSGPSC

Results of Swiss-Modeler

Batch.1:  residues 33 - 77 of submitted sequence.
Batch.2:  residues 1 - 76 of submitted sequence.
Batch.3:  residues 33 - 119 of submitted sequence.
Batch.4:  residues 77 - 192 of submitted sequence.

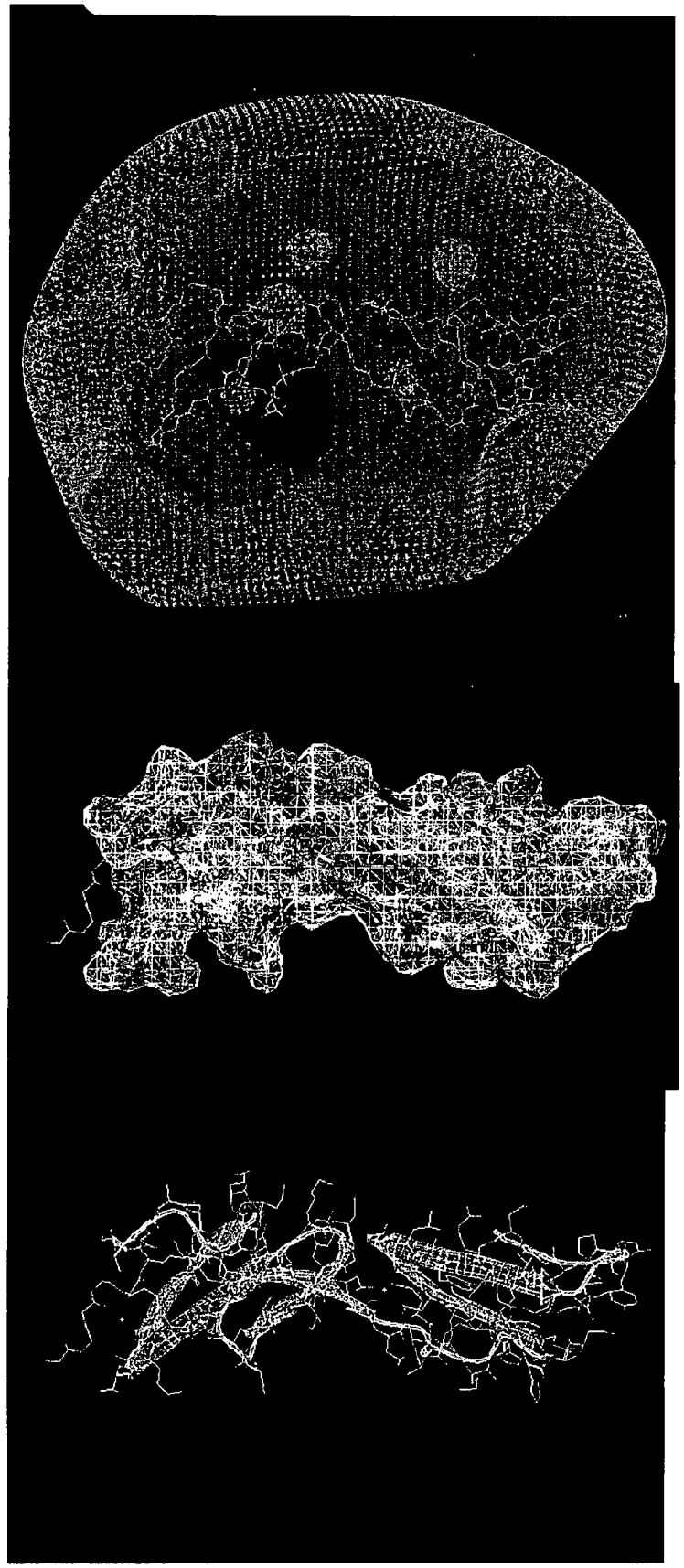

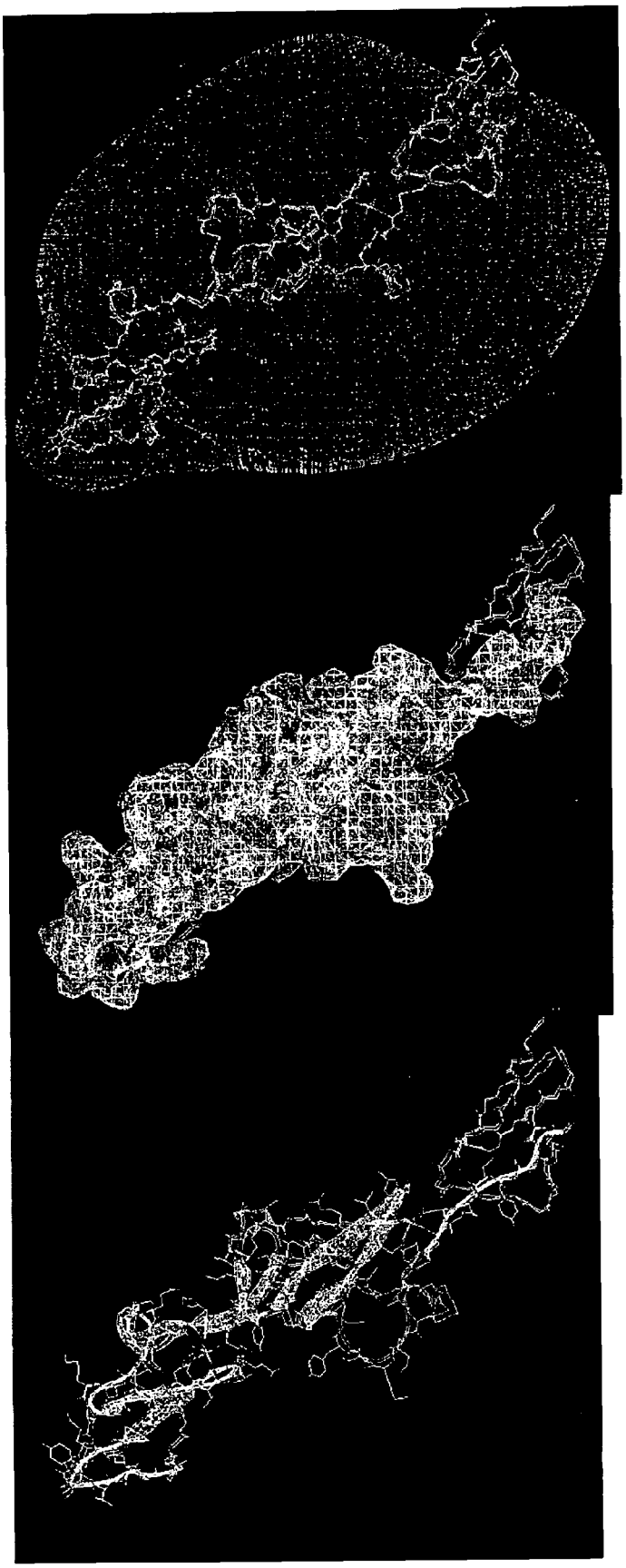

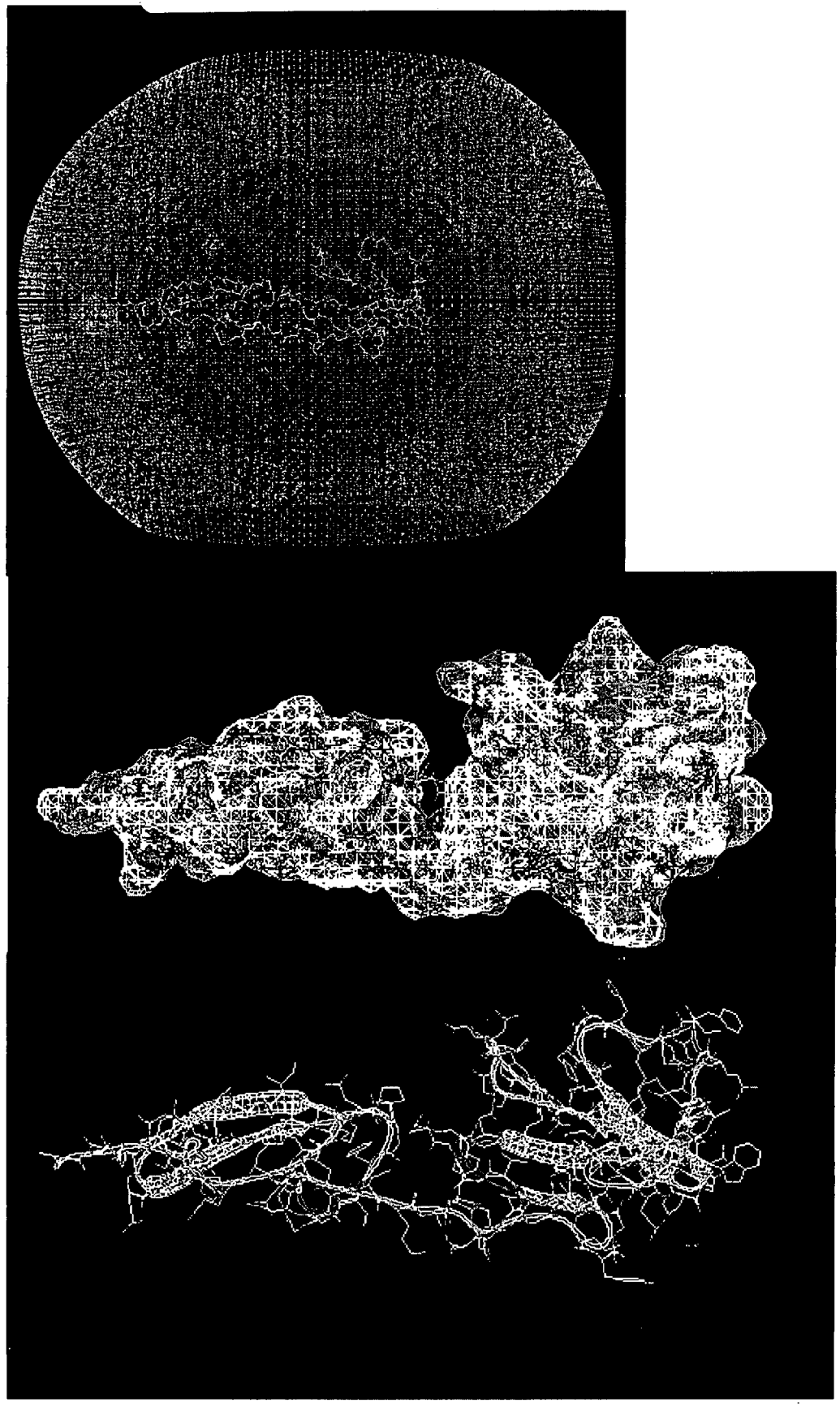

SEQUENCE LISTING

```
<160> NUMBER OF SEQ ID NOS: 8

<210> SEQ ID NO 1
<211> LENGTH: 810
<212> TYPE: PRT
<213> ORGANISM: Homo sapiens

<400> SEQUENCE: 1

Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
            20                  25                  30

Val Thr Glu Leu Asp Leu Val Asn Thr Thr Leu Gly Val Ala Gln Val
        35                  40                  45

Ser Gly Met His Asn Ala Ser Lys Ala Phe Leu Phe Gln Asp Ile Glu
    50                  55                  60

Arg Glu Ile His Ala Ala Pro His Val Ser Glu Lys Leu Ile Gln Leu
65                  70                  75                  80

Phe Gln Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
```

-continued

```
            210                 215                 220
His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
                260                 265                 270

Cys Gln Val Ser Gly Leu Leu Tyr Arg Asp Gln Asp Ser Trp Val Asp
                275                 280                 285

Gly Asp His Cys Arg Asn Cys Thr Cys Lys Ser Gly Ala Val Glu Cys
290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
                340                 345                 350

Cys Arg Glu Cys Arg Gly Gly Val Leu Val Lys Ile Thr Glu Met Cys
                355                 360                 365

Pro Pro Leu Asn Cys Ser Glu Lys Asp His Ile Leu Pro Glu Asn Gln
                370                 375                 380

Cys Cys Arg Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
                405                 410                 415

Glu Cys Lys Ser Gly Tyr Ile Ser Val Gln Gly Asp Ser Ala Tyr Cys
                420                 425                 430

Glu Asp Ile Asp Glu Cys Ala Ala Lys Met His Tyr Cys His Ala Asn
                435                 440                 445

Thr Val Cys Val Asn Leu Pro Gly Leu Tyr Arg Cys Asp Cys Val Pro
450                 455                 460

Gly Tyr Ile Arg Val Asp Asp Phe Ser Cys Thr Glu His Asp Glu Cys
465                 470                 475                 480

Gly Ser Gly Gln His Asn Cys Asp Glu Asn Ala Ile Cys Thr Asn Thr
                485                 490                 495

Val Gln Gly His Ser Cys Thr Cys Lys Pro Gly Tyr Val Gly Asn Gly
                500                 505                 510

Thr Ile Cys Arg Ala Phe Cys Glu Glu Gly Cys Arg Tyr Gly Gly Thr
                515                 520                 525

Cys Val Ala Pro Asn Lys Cys Val Cys Pro Ser Gly Phe Thr Gly Ser
530                 535                 540

His Cys Glu Lys Asp Ile Asp Glu Cys Ser Glu Gly Ile Ile Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
                580                 585                 590

Ser Cys Ile Asp Ile Asp Glu Cys Ala Leu Arg Thr His Thr Cys Trp
                595                 600                 605

Asn Asp Ser Ala Cys Ile Asn Leu Ala Gly Gly Phe Asp Cys Leu Cys
610                 615                 620

Pro Ser Gly Pro Ser Cys Ser Gly Asp Cys Pro His Glu Gly Gly Leu
625                 630                 635                 640
```

```
Lys His Asn Gly Gln Val Trp Thr Leu Lys Glu Asp Arg Cys Ser Val
                645                 650                 655
Cys Ser Cys Lys Asp Gly Lys Ile Phe Cys Arg Arg Thr Ala Cys Asp
            660                 665                 670
Cys Gln Asn Pro Ser Ala Asp Leu Phe Cys Cys Pro Glu Cys Asp Thr
        675                 680                 685
Arg Val Thr Ser Gln Cys Leu Asp Gln Asn Gly His Lys Leu Tyr Arg
    690                 695                 700
Ser Gly Asp Asn Trp Thr His Ser Cys Gln Gln Cys Arg Cys Leu Glu
705                 710                 715                 720
Gly Glu Val Asp Cys Trp Pro Leu Thr Cys Pro Asn Leu Ser Cys Glu
                725                 730                 735
Tyr Thr Ala Ile Leu Glu Gly Glu Cys Cys Pro Arg Cys Val Ser Asp
            740                 745                 750
Pro Cys Leu Ala Asp Asn Ile Thr Tyr Asp Ile Arg Lys Thr Cys Leu
        755                 760                 765
Asp Ser Tyr Gly Val Ser Arg Leu Ser Gly Ser Val Trp Thr Met Ala
    770                 775                 780
Gly Ser Pro Cys Thr Thr Cys Lys Cys Lys Asn Gly Arg Val Cys Cys
785                 790                 795                 800
Ser Val Asp Phe Glu Cys Leu Gln Asn Asn
                805                 810

<210> SEQ ID NO 2
<211> LENGTH: 2977
<212> TYPE: DNA
<213> ORGANISM: Homo sapiens

<400> SEQUENCE: 2
tagcaagttt ggcggctcca agccaggcgc gcctcaggat ccaggctcat ttgcttccac     60
ctagcttcgg tgcccctgc taggcgggga ccctcgagag cgatgccgat ggatttgatt    120
ttagttgtgt ggttctgtgt gtgcactgcc aggacagtgg tgggctttgg gatggaccct    180
gaccttcaga tggatatcgt caccgagctt gaccttgtga caccaccct tggagttgct    240 caggtgtctg gaatgcacaa tgccagcaaa gcatttttat ttcaagacat agaaagagag    300
atccatgcag ctcctcatgt gagtgagaaa ttaattcagc tgttccagaa caagagtgaa    360
ttcaccattt tggccactgt acagcagaag ccatccactt caggagtgat actgtccatt    420
cgagaactgg agcacagcta ttttgaactg gagagcagtg cctgaggga tgagattcgg    480 tatcactaca tacacaatgg gaagccaagg acagaggcac ttccttaccg catggcagat    540
ggacaatggc acaaggttgc actgtcagtt agcgcctctc atctcctgct ccatgtcgac    600
tgtaacagga tttatgagcg tgtgatagac cctccagata ccaaccttcc cccaggaatc    660
aatttatggc ttggccagcg caaccaaaag catggcttat tcaaagggat catccaagat    720
gggaagatca tctttatgcc gaatggatat ataacacagt gtccaaatct aaatcacact    780
tgcccaacct gcagtgattt cttaagcctg gtgcaaggaa taatggattt acaagagctt    840
ttggccaaga tgactgcaaa actaaattat gcagagacaa gacttagtca attggaaaac    900
tgtcattgtg agaagacttg tcaagtgagt ggactgctct atcgagatca agactcttgg    960
gtagatggtg accattgcag gaactgcact tgcaaaagtg gtgccgtgga atgccgaagg    1020
atgtcctgtc cccctctcaa ttgctcccca gactccctcc cagtacacat tgctggccag    1080
tgctgtaagg tctgccgacc aaaatgtatc tatgaggaa aagttcttgc agaaggccag    1140
```

-continued

```
cggattttaa ccaagagctg tcgggaatgc cgaggtggag ttttagtaaa aattacagaa    1200
atgtgtcctc ctttgaactg ctcagaaaag gatcacattc ttcctgagaa tcagtgctgc    1260
cgtgtctgta gaggtcataa cttttgtgca aaggaccta aatgtggtga aaactcagag    1320
tgcaaaaact ggaatacaaa agctacttgt gagtgcaaga gtggttacat ctctgtccag    1380
ggagactctg cctactgtga agatattgat gagtgtgcag ctaagatgca ttactgtcat    1440
gccaatactg tgtgtcaa ccttcctggg ttatatcgct gtgactgtgt cccaggatac    1500
attcgtgtgg atgacttctc ttgtacagaa acgatgaat gtggcagcgg ccagcacaac    1560
tgtgatgaga atgccatctg caccaacact gtccagggac acagctgcac ctgcaaaccg    1620
ggctacgtgg ggaacgggac catctgcaga gctttctgtg aagagggctg cagatacggt    1680
ggaacgtgtg tggctcccaa caaatgtgtc tgtccatctg gattcacagg aagccactgc    1740
gagaaagata ttgatgaatg ttcagaggga atcattgagt gccacaacca ttcccgctgc    1800
gttaacctgc agggtggta ccactgtgag tgcagaagcg gtttccatga cgatgggacc    1860
tattcactgt ccggggagtc ctgtattgac attgatgaat gtgccttaag aactcacacc    1920
tgttggaacg attctgcctg catcaacctg cagggggtt ttgactgtct ctgcccctct    1980
gggccctcct gctctggtga ctgtcctcat gaagggggggc tgaagcacaa tggccaggtg    2040
tggaccttga agaagacag gtgttctgtc tgctcctgca aggatggcaa gatattctgc    2100
cgacggacag cttgtgattg ccagaatcca agtgctgacc tattctgttg cccagaatgt    2160
gacaccagag tcacaagtca atgtttagac caaaatggtc acaagctgta tcgaagtgga    2220
gacaattgga cccatagctg tcagcagtgt cggtgtctgg aaggagaggt agattgctgg    2280
ccactcactt gccccaactt gagctgtgag tatacagcta tcttagaagg ggaatgttgt    2340
ccccgctgtg tcagtgaccc ctgcctagct gataacatca cctatgacat cagaaaaact    2400
tgcctggaca gctatggtgt ttcacggctt agtggctcag tgtggacgat ggctggatct    2460
ccctgcacaa cctgtaaatg caagaatgga agagtctgtt gttctgtgga ttttgagtgt    2520
cttcaaaata attgaagtat ttacagtgga ctcaacgcag aagaatggac gaaatgacca    2580
tccaacgtga ttaaggatag gaatcggtag tttggttttt ttgtttgttt tgttttttta    2640
accacagata attgccaaag tttccacctg aggacggtgt ttcggaggtt gccttttgga    2700
cctaccactt tgctcattct tgctaaccta gtctaggtga cctacagtgc cgtgcattta    2760
agtcaatggt tgttaaaaga gtttcccgt gttgtaaatc atgtttccct tatcagatca    2820
tttgcaaata catttaaatg atctcatggt aaatggttga tgtatttttt gggtttattt    2880
tgtgtactaa ccataataga gagagactca gctcctttta tttattttgt tgatttatgg    2940
atcaaattct aaaataaagt tgcctgttgt gactttt                            2977
```

<210> SEQ ID NO 3
<211> LENGTH: 810
<212> TYPE: PRT
<213> ORGANISM: Rattus sp.

<400> SEQUENCE: 3

| Met | Pro | Met | Asp | Val | Ile | Leu | Val | Leu | Trp | Phe | Cys | Val | Cys | Thr | Ala |
|---|---|---|---|---|---|---|---|---|---|---|---|---|---|---|---|
| 1 | | | | 5 | | | | | 10 | | | | | 15 | |

| Arg | Thr | Val | Leu | Gly | Phe | Gly | Met | Asp | Pro | Asp | Leu | Gln | Leu | Asp | Ile |
|---|---|---|---|---|---|---|---|---|---|---|---|---|---|---|---|
| | | | 20 | | | | | 25 | | | | | 30 | | |

| Ile | Ser | Glu | Leu | Asp | Leu | Val | Asn | Thr | Thr | Leu | Gly | Val | Thr | Gln | Val |
|---|---|---|---|---|---|---|---|---|---|---|---|---|---|---|---|
| | 35 | | | | | 40 | | | | | 45 | | | | |

```
Ala Gly Leu His Asn Ala Ser Lys Ala Phe Leu Phe Gln Asp Val Gln
     50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Pro Pro Tyr Arg Met
    130                 135                 140

Ala Asp Gly Gln Trp His Lys Val Ala Leu Ser Val Ser Ala Ser His
145                 150                 155                 160

Leu Leu Leu His Ile Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
            340                 345                 350

Cys Arg Glu Cys Arg Gly Gly Val Leu Val Lys Ile Thr Glu Ala Cys
        355                 360                 365

Pro Pro Leu Asn Cys Ser Ala Lys Asp His Ile Leu Pro Glu Asn Gln
    370                 375                 380

Cys Cys Arg Val Cys Pro Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asn Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Val Pro
    450                 455                 460
```

```
Gly Tyr Ile Arg Val Asp Asp Phe Ser Cys Thr Glu His Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510

Thr Ile Cys Lys Ala Phe Cys Glu Glu Gly Cys Arg Tyr Gly Gly Thr
        515                 520                 525

Cys Val Ala Pro Asn Lys Cys Val Cys Pro Ser Gly Phe Thr Gly Ser
    530                 535                 540

His Cys Glu Lys Asp Ile Asp Glu Cys Ala Glu Gly Phe Val Glu Cys
545                 550                 555                 560

His Asn Tyr Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
    690                 695                 700

Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Gly Cys Glu
                725                 730                 735

Tyr Thr Ala Met Phe Glu Gly Cys Cys Pro Arg Cys Val Ser Asp
            740                 745                 750

Pro Cys Leu Ala Asp Asn Ile Ala Tyr Asp Ile Arg Lys Thr Cys Leu
        755                 760                 765

Asp Ser Phe Gly Val Ser Arg Leu Ser Gly Ala Val Trp Thr Met Ala
    770                 775                 780

Gly Ser Pro Cys Thr Thr Cys Lys Cys Lys Asn Gly Arg Val Cys Cys
785                 790                 795                 800

Ser Val Asp Leu Glu Cys Ile Glu Asn Asn
                805                 810

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Glu Ala Leu Pro Tyr Arg Met Ala Asp Gly Gln Trp His Lys Val Ala
1               5                   10                  15
```

Leu Cys

<210> SEQ ID NO 5
<211> LENGTH: 100
<212> TYPE: PRT
<213> ORGANISM: Artificial Sequence
<220> FEATURE:
<223> OTHER INFORMATION: Synthetic peptide

<400> SEQUENCE: 5

Cys Arg Arg Met Ser Cys Pro Pro Leu Asn Cys Ser Pro Asp Ser Leu
1               5                   10                  15

Pro Val His Ile Ala Gly Gln Cys Lys Val Cys Arg Pro Lys Cys
            20                  25                  30

Ile Tyr Gly Gly Lys Val Leu Ala Glu Gly Gln Arg Ile Leu Thr Lys
        35                  40                  45

Ser Cys Arg Glu Cys Arg Gly Gly Val Leu Val Lys Ile Thr Glu Met
    50                  55                  60

Cys Pro Pro Leu Asn Cys Ser Glu Lys Asp His Ile Leu Pro Glu Asn
65                  70                  75                  80

Gln Cys Cys Arg Val Cys Arg Gly His Asn Phe Cys Ala Glu Gly Pro
                85                  90                  95

Lys Cys Gly Glu
            100

<210> SEQ ID NO 6
<211> LENGTH: 236
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: Sequence of 6-EGF like repeats

<400> SEQUENCE: 6

Cys Ala Glu Ala Pro Lys Cys Gly Glu Asn Ser Glu Cys Lys Asn Trp
1               5                   10                  15

Asn Thr Lys Ala Thr Cys Glu Cys Lys Asn Gly Tyr Ile Ser Val Gln
            20                  25                  30

Gly Asn Ser Ala Tyr Cys Glu Asp Ile Asp Glu Cys Ala Ala Lys Met
        35                  40                  45

His Tyr Cys His Ala Asn Thr Val Cys Val Asn Leu Pro Gly Leu Tyr
    50                  55                  60

Arg Cys Asp Cys Val Pro Gly Tyr Ile Arg Val Asp Asp Phe Ser Cys
65                  70                  75                  80

Thr Glu His Asp Asp Cys Gly Ser Gly Gln His Asn Cys Asp Lys Asn
                85                  90                  95

Ala Ile Cys Thr Asn Thr Val Gln Gly His Ser Cys Thr Cys Gln Pro
            100                 105                 110

Gly Tyr Val Gly Asn Gly Thr Ile Cys Lys Ala Phe Cys Glu Glu Gly
        115                 120                 125

Cys Arg Tyr Gly Gly Thr Cys Val Ala Pro Asn Lys Cys Val Cys Pro
    130                 135                 140

Ser Gly Phe Thr Gly Ser His Cys Glu Lys Asp Ile Asp Glu Cys Ala
145                 150                 155                 160

Glu Gly Phe Val Glu Cys His Asn Tyr Ser Arg Cys Val Asn Leu Pro
                165                 170                 175

```
Gly Trp Tyr His Cys Glu Cys Arg Ser Gly Phe His Asp Asp Gly Thr
            180                 185                 190

Tyr Ser Leu Ser Gly Glu Ser Cys Ile Asp Ile Asp Glu Cys Ala Leu
            195                 200                 205

Arg Thr His Thr Cys Trp Asn Asp Ser Ala Cys Ile Asn Leu Ala Gly
        210                 215                 220

Gly Phe Asp Cys Leu Cys Pro Ser Gly Pro Ser Cys
225                 230                 235

<210> SEQ ID NO 7
<211> LENGTH: 1722
<212> TYPE: DNA
<213> ORGANISM: Homo sapiens
<220> FEATURE:
<221> NAME/KEY: misc_feature
<223> OTHER INFORMATION: Genbank Accession No. U57523
<220> FEATURE:
<221> NAME/KEY: misc_feature
<222> LOCATION: (1594)..(1594)
<223> OTHER INFORMATION: n is a, c, g, or t
<220> FEATURE:
<221> NAME/KEY: misc_feature
<222> LOCATION: (1655)..(1655)
<223> OTHER INFORMATION: n is a, c, g, or t
<220> FEATURE:
<221> NAME/KEY: misc_feature
<222> LOCATION: (1657)..(1657)
<223> OTHER INFORMATION: n is a, c, g, or t
<220> FEATURE:
<221> NAME/KEY: misc_feature
<222> LOCATION: (1697)..(1697)
<223> OTHER INFORMATION: n is a, c, g, or t
<220> FEATURE:
<221> NAME/KEY: misc_feature
<222> LOCATION: (1720)..(1720)
<223> OTHER INFORMATION: n is a, c, g, or t

<400> SEQUENCE: 7
gatcagtgct gccgtgtctg tagaggtcat aacttttgtg cagaaggacc taaatgtggt      60
gaaaactcag agtgcaaaaa ctggaataca aaagctactt gtgagtgcaa gagtggttac     120
atctctgtcc aggggagact ctgcctactg tgaagatatt gatgagtgtg cagctaagat     180
gcattactgt catgccaata ctgtgtgtgt caaccttcct gggttatatc gctgtgactg     240
tgtcccagga tacattcgtg tggatgactt ctcttgtaca gaacacgatg aatgtggcag     300
cggccagcac aactgtgatg agaatgccat ctgcaccaac actgtccagg gacacagctg     360
cacctgcaaa ccgggctacg tggggaacgg gaccatctgc agagcttttct gtgaagaggg     420 ctgcagatac ggtggaacgt gtgtggctcc aacaaatgt gtctgtccat ctggattcac     480
aggaagccac tgcgagaaag atattgatga atgttcagag ggaatcattg agtgccacaa     540
ccattcccgc tgcgttaacc tgccagggtg caccactgt gagtgcagaa gcggtttcca     600
tgacgatggg acctattcac tgtccgggga gtcctgtatt gacattgatg aatgtgcctt     660
aagaactcac acctgttgga acgattctgc ctgcatcaac ctggcagggg gttttgactg     720
tctctgcccc tgtgggccct cctgctctgg tgactgtcct catgaagggg ggctgaagca     780
caatggccag gtgtggacct tgaaagaaga caggtgttct gtctgctcct gcaaggatgg     840
taagatattc tgccgacgga cagcttgtga ttgccagaat ccaagtgctg acctattctg     900
ttgcccagaa tgtgacacca gagtcacaag tcaatgttta gaccaaaatg gtcacaagct     960
gtatcgaagt ggagacaatt ggacccatag ctgtcagcag gtcggtgtc tggaaggaga    1020 ggtagattgc tggccactca cttgcccaa cttgagctgt gagtatacag ctatcttaga    1080
```

-continued

```
agggaatgt tgtccccgct gtgtcagtga cccctgccta gctgataaca tcacctatga   1140
catcagaaaa acttgcctgg acagtatggt gtttcacggc ttagtggctc agtgtggacg   1200
atggctggat ctccctgcac aacctgtaaa tgcaagaatg gaagagtctg ttgttctgtg   1260
gattttgagt gtcttcaaaa taattgaagt atttacagtg gactcaacgc agaagaatgg   1320
acgaaatgac catccaacgt gattaaggat aggaatcggt agtttggttt ttttgtttgt   1380
tttgtttttt taaccacaga taattgccaa agtttccacc tgaggacggt gtttggaggt   1440
tgccttttgg acctaccact ttgctcattc ttgctaacct agtttaggtg acctacagtg   1500
ccgtgcattt aagtcagtgg ttgttaaaag aagtttcccg cgttgtaaat catgtttccc   1560
ttatcagatc atttgcaaat acatttaaat gatntcatgg taaatgttgc tgtattttt    1620 ggtttattt ctgtactaac ataatagaga gagantnagc tccttttatt tattttgttg    1680
atttatggat caaattntaa aataaagttg cctgttgtgn aa                     1722
```

<210> SEQ ID NO 8
<211> LENGTH: 446
<212> TYPE: PRT
<213> ORGANISM: Homo sapiens
<220> FEATURE:
<221> NAME/KEY: misc_feature
<223> OTHER INFORMATION: Protein resulting from CDS of SEQ ID NO: 7

<400> SEQUENCE: 8

```
Ile Ser Ala Ala Val Ser Val Glu Val Ile Thr Phe Val Gln Lys Asp
1               5                   10                  15

Leu Asn Val Val Lys Thr Gln Ser Ala Lys Thr Gly Ile Gln Lys Leu
            20                  25                  30

Leu Val Ser Ala Arg Val Val Thr Ser Leu Ser Arg Gly Asp Ser Ala
        35                  40                  45

Tyr Cys Glu Asp Ile Asp Glu Cys Ala Ala Lys Met His Tyr Cys His
    50                  55                  60

Ala Asn Thr Val Cys Val Asn Leu Pro Gly Leu Tyr Arg Cys Asp Cys
65                  70                  75                  80

Val Pro Gly Tyr Ile Arg Val Asp Asp Phe Ser Cys Thr Glu His Asp
                85                  90                  95

Glu Cys Gly Ser Gly Gln His Asn Cys Asp Glu Asn Ala Ile Cys Thr
            100                 105                 110

Asn Thr Val Gln Gly His Ser Cys Thr Cys Lys Pro Gly Tyr Val Gly
        115                 120                 125

Asn Gly Thr Ile Cys Arg Ala Phe Cys Glu Glu Gly Cys Arg Tyr Gly
    130                 135                 140

Gly Thr Cys Val Ala Pro Asn Lys Cys Val Cys Pro Ser Gly Phe Thr
145                 150                 155                 160

Gly Ser His Cys Glu Lys Asp Ile Asp Glu Cys Ser Glu Gly Ile Ile
                165                 170                 175

Glu Cys His Asn His Ser Arg Cys Val Asn Leu Pro Gly Trp His His
            180                 185                 190

Cys Glu Cys Arg Ser Gly Phe His Asp Asp Gly Thr Tyr Ser Leu Ser
        195                 200                 205

Gly Glu Ser Cys Ile Asp Ile Asp Glu Cys Ala Leu Arg Thr His Thr
    210                 215                 220

Cys Trp Asn Asp Ser Ala Cys Ile Asn Leu Ala Gly Gly Phe Asp Cys
225                 230                 235                 240

Leu Cys Pro Cys Gly Pro Ser Cys Ser Gly Asp Cys Pro His Glu Gly
```

-continued

```
            245                 250                 255
Gly Leu Lys His Asn Gly Gln Val Trp Thr Leu Lys Glu Asp Arg Cys
            260                 265                 270

Ser Val Cys Ser Cys Lys Asp Gly Lys Ile Phe Cys Arg Arg Thr Ala
            275                 280                 285

Cys Asp Cys Gln Asn Pro Ser Ala Asp Leu Phe Cys Cys Pro Glu Cys
            290                 295                 300

Asp Thr Arg Val Thr Ser Gln Cys Leu Asp Gln Asn Gly His Lys Leu
305                     310                 315                 320

Tyr Arg Ser Gly Asp Asn Trp Thr His Ser Cys Gln Gln Cys Arg Cys
                325                 330                 335

Leu Glu Gly Glu Val Asp Cys Trp Pro Leu Thr Cys Pro Asn Leu Ser
                340                 345                 350

Cys Glu Tyr Thr Ala Ile Leu Glu Gly Glu Cys Cys Pro Arg Cys Val
            355                 360                 365

Ser Asp Pro Cys Leu Ala Asp Asn Ile Thr Tyr Asp Ile Arg Lys Thr
    370                 375                 380

Cys Leu Asp Ser Met Val Phe His Gly Leu Val Ala Gln Cys Gly Arg
385                 390                 395                 400

Trp Leu Asp Leu Pro Ala Gln Pro Val Asn Ala Arg Met Glu Glu Ser
                405                 410                 415

Val Val Leu Trp Ile Leu Ser Val Phe Lys Ile Ile Glu Val Phe Thr
                420                 425                 430

Val Asp Ser Thr Gln Lys Asn Gly Arg Asn Asp His Pro Thr
            435                 440                 445
```

NELL-1 ENHANCED BONE MINERALIZATION

CROSS-REFERENCE TO RELATED APPLICATIONS

This application is also a continuation-in-part of U.S. application Ser. No. 11/392,294, filed on Mar. 28, 2006, which is a continuation application of U.S. application Ser. No. 09/412,297, filed on Oct. 5, 1999, issued as U.S. Pat. No. 7,052,856. It is also a continuation-in-part of U.S. application Ser. No. 10/544,553, filed May 15, 2006, issued as U.S. Pat. No. 7,544,486, which is a U.S. National Phase of PCT application PCT/US2004/003808, filed on Feb. 9, 2004, the teachings of which are incorporated herein by reference.

STATEMENT AS TO RIGHTS TO INVENTIONS MADE UNDER FEDERALLY SPONSORED RESEARCH AND DEVELOPMENT

This invention was made with Government support under Grant Nos. DE000422, DE014649, DE094001, and RR000865 awarded by the National Institutes of Health. The Government has certain rights in this invention.

FIELD OF THE INVENTION

This application generally relates to NELL-1 peptides and methods of using the peptide or a composition thereof for enhancing bone mineralization for bone regeneration and/bone repair.

BACKGROUND OF THE INVENTION

Defects in the process of bone repair and regeneration are linked to the development of several human diseases and disorders, e.g. osteoporosis and osteogenesis imperfecta. Failure of the bone repair or cartilage repair mechanism is also associated with significant complications in clinical orthopedic practice, for example, fibrous non-union following bone fracture, implant interface failures and large allograft failures. The lives of many individuals would be improved by the development of new therapies designed to stimulate and strengthen the fracture repair process.

Any new technique to stimulate bone repair or cartilage repair would be a valuable tool in treating bone fractures. A significant portion of fractured bones are still treated by casting, allowing natural mechanisms to effect wound repair. Although there have been advances in fracture treatment in recent years, including improved devices, the development of new processes to stimulate, or complement, the wound repair mechanisms would represent significant progress in this area. For example, efforts to influence bone repair using bone stimulating proteins and peptides, e.g., bone morphogenic proteins (BMPs), resulted in only limited success.

Therefore, there is a need for agents and compositions for enhancing bone mineralization for bone regeneration and repair.

Therefore, there is a need for agents and compositions for enhancing cartilage regeneration and repair.

The embodiments described below address the above issues and needs.

SUMMARY OF THE INVENTION

This invention describes an osteogenic polypeptide (NELL-1) encoded by the human NELL-1 gene for bone mineralization. The NELL-1 gene and gene product(s) (e.g. mRNA, cDNA, protein, etc.) provide good targets for screening for modulators of NELL-1 expression and/or activity and therefore for modulators of bone formation. In addition, NELL-1 gene can be used to enhance fracture repair, e.g., as a component of bone graft or bone graft substitute materials or as a stand alone agent without bone graft or bone graft substitute materials.

In some embodiments, this invention provides methods of screening for an agent that alters bone mineralization. The methods involve contacting a cell containing a NELL-1 gene with a test agent; and detecting a change in the expression level of the NELL-1 gene as compared to the expression of the NELL-1 gene in a cell that is not contacted with the test agent where a difference in the expression level (e.g. as represented by genomic DNA copy number, mRNA level, protein level, protein activity, etc.), of NELL-1 in the contacted cell and the cell that is not contacted indicates that the agent modulates bone mineralization. The methods further involve test agents that alter expression of the NELL-1 nucleic acid or the NELL-1 protein in a database of modulators of NELL-1 activity or in a database of modulators of bone mineralization. In certain embodiments, the expression level of NELL-1 is detected by measuring the level of NELL-1 mRNA in the cell (e.g. by hybridizing the mRNA to a probe that specifically hybridizes to a NELL-1 nucleic acid). Preferred hybridization methods include, but are not limited to a Northern blot, a Southern blot using DNA derived from the NELL-1 RNA, an array hybridization, an affinity chromatography, and an in situ hybridization. The methods of this invention are amenable to array-based approaches. Thus, in some embodiments, the probe is a member of a plurality of probes that forms an array of probes. The level of NELL-1 expression can also be determined using a nucleic acid amplification reaction (e.g. PCR).

In other embodiments, NELL-1 expression can be detected by determining the expression level of a NELL-1 protein (e.g. via of capillary electrophoresis, a Western blot, mass spectroscopy, ELISA, immunochromatography, immunohistochemistry, etc.) in the biological sample. The cell can be cultured ex vivo or can be in vivo and/or in situ. In certain embodiments, the test agent is not an antibody and/or not a protein and/or not a nucleic acid. Preferred test agents are small organic molecules.

In some other embodiments, this invention provides methods of prescreening for a potential modulator of NELL-1 expression and/or activity. The methods involve contacting a NELL-1 nucleic acid or a NELL-1 protein with a test agent; and detecting specific binding of the test agent to the NELL-1 protein or nucleic acid. The method can further involve recording test agents that specifically bind to the NELL-1 nucleic acid or to the NELL-1 protein in a database of candidate modulators of NELL-1 gene or protein activity and/or in a database of candidate modulators of bone mineralization. The test agent can be contacted directly to the NELL-1 nucleic acid and/or protein, or to a cell and/or tissue and/or organism (e.g. mammal) containing the nucleic acid and/or protein. Where a cell is contacted, the cell can be in a primary or passaged culture. In certain embodiments, the test agent is not an antibody and/or not a protein and/or not a nucleic acid. Preferred test agents are small organic molecules. Where the assay measures the ability of the test agent to bind to a nucleic acid, preferred assays utilize a Northern blot, a Southern blot using DNA, an array hybridization, an affinity chromatography, or an in situ hybridization. Where the assay measures the ability of the test agent to bind to a NELL-1 protein, preferred assays utilize capillary electrophoresis, a Western blot, mass spectroscopy, ELISA, immunochromatography, or immunohistochemistry).

In another embodiment, this invention provides methods of increasing bone mineralization. Preferred methods involve increasing the concentration of a NELL-1 gene product in an osteogenic cell (e.g. an osteoblast, a mesenchymal cell, a fibroblast cell, a fetal embryonic cell, a stem cell, a bone marrow cell, a dura cell, a chrondrocyte, a chondroblast, etc.) or in the milieu within which the cell is found. In one preferred embodiment, the concentration of NELL-1 gene product is increased by upregulating expression of a NELL-1 gene. This can be accomplished by any of a wide variety of methods including, but not limited to upregulating expression of an endogenous NELL-1 gene (e.g. by modifying the endogenous regulatory region e.g. the promoter), or transfecting the cell with a vector that expresses a NELL-1 protein. Certain preferred vectors constitutively express a NELL-1 protein, while other preferred vectors are inducible. In still another embodiment, the NELL-1 gene product concentration is increased by the bone with a NELL-1 polypeptide.

This invention also provides methods of facilitating the repair of bone fractures. These methods involve increasing concentration of a NELL-1 gene product at or near the fracture site. In preferred embodiments, the NELL-1 gene product is increased in an osteogenic or bone precursor cell present at or near the fracture site. The methods can involve introducing an osteogenic cell or bone precursor cell that overexpresses NELL-1 into the fracture site. In another embodiment, this invention can involve increasing the concentration of a NELL-1 gene product in the osteogenic cell or the bone precursor cell in situ. The NELL-1 gene product up-regulation can be achieved as described herein. In another embodiment, the cell and/or bone fracture site is contacted with a NELL-1 polypeptide.

In another approach to fracture repair, the fracture site is contacted with a NELL-1 protein. The protein can be produced by a cell (e.g. introduced by introduction of a cell overexpressing NELL-1 protein) and/or by administration of the protein alone or in combination with a pharmacological excipient, and/or by administration of a "naked DNA" vector capable of expressing NELL-1. The NELL-1 protein can be a component of a bone repair/bone graft material and/or part of a prosthetic device. One preferred graft material includes collagen and/or demineralized or non-demineralized bone fragments in addition to the NELL-1 protein and/or cells expressing a NELL-1 protein.

In still yet another embodiment this invention provides a bone or cartilage graft material or a pharmaceutical composition for enhancing the formation of osseous tissue in the animal in which it is implanted. Preferred bone or cartilage graft materials contain a biocompatible matrix and a NELL-1 protein, a NELL-1 related agent, or combinations thereof. A preferred graft material is resorbable/biodegradable. A preferred graft material can be synthetic or naturally occurring (e.g., allograft). The matrix can include a biodegradable polymer and can be impregnated with a NELL-1 protein, a NELL-1 related agent, and/or a cell expressing a NELL-1 protein or a NELL-1 related agent. An exemplary bone graft material comprises a collagen conjugate containing: (e.g. from about 0.001 to about 99.999 weight percent) collagen having dispersed substantially uniformly therein; and (e.g. about 99.999 to about 0.001 weight percent) a NELL-1 protein, a NELL-1 related agent, and/or a cell expressing a NELL-1 protein or a NELL-1 related agent.

BRIEF DESCRIPTION OF THE DRAWINGS

FIG. 1A illustrates over-expression of NELL-1 in E-14 rat calvarial primary cell cultures using adenoviruses with beta-galactosidase as control. FIG. 1B shows a plot of mineralization as a function of time post treatment with NELL-1 and beta-glactosidase respectively. Experiments were performed in triplicate. Student's T test was performed. Mineralization with NELL-1 was statistically higher than mineralization with beta.-Galactosidase control, *$P<0.001$.

FIG. 2 shows schematic structures of rat NELL-1 protein and mouse thrombospondin (TSP)-1. All Nel-like molecules contain several highly conserved motifs including a secretory signal peptide, an $NH_2$-terminal thrombospondin-1 (TSP-1)-like module, five chordin-like cysteine-rich (CR) domains and six epidermal growth factor (EGF)-like domains. The 130-kDa monomers are assumed to associate into homotrimers via either the coiled-coil region or CR domains. Signal peptide region (solid black box), TSP-N modules (TSP-N, shaded box), cysteine-rich (CR) domains (CR, solid white boxes), epidermal growth factor (EGF)-like domains (E, hatched boxes), coiled-coil regions (CC, bars), $Ca2+$-binding type EGF-like domains (*), and RGD peptide domains (RGD, solid white box) are indicated.

FIG. 3 shows the amino acid sequences comprising each of the domains shown in FIG. 2. (SEQ ID NOS: 3-5).

FIGS. 4A-4D are a computer models of partial NELL-1 structure (e.g., the six EGF-like domains (SEQ ID NOS: 6)) generated using computer programs known to those in the art (e.g., Swiss-Model).

DETAILED DESCRIPTION

Figure 4A:
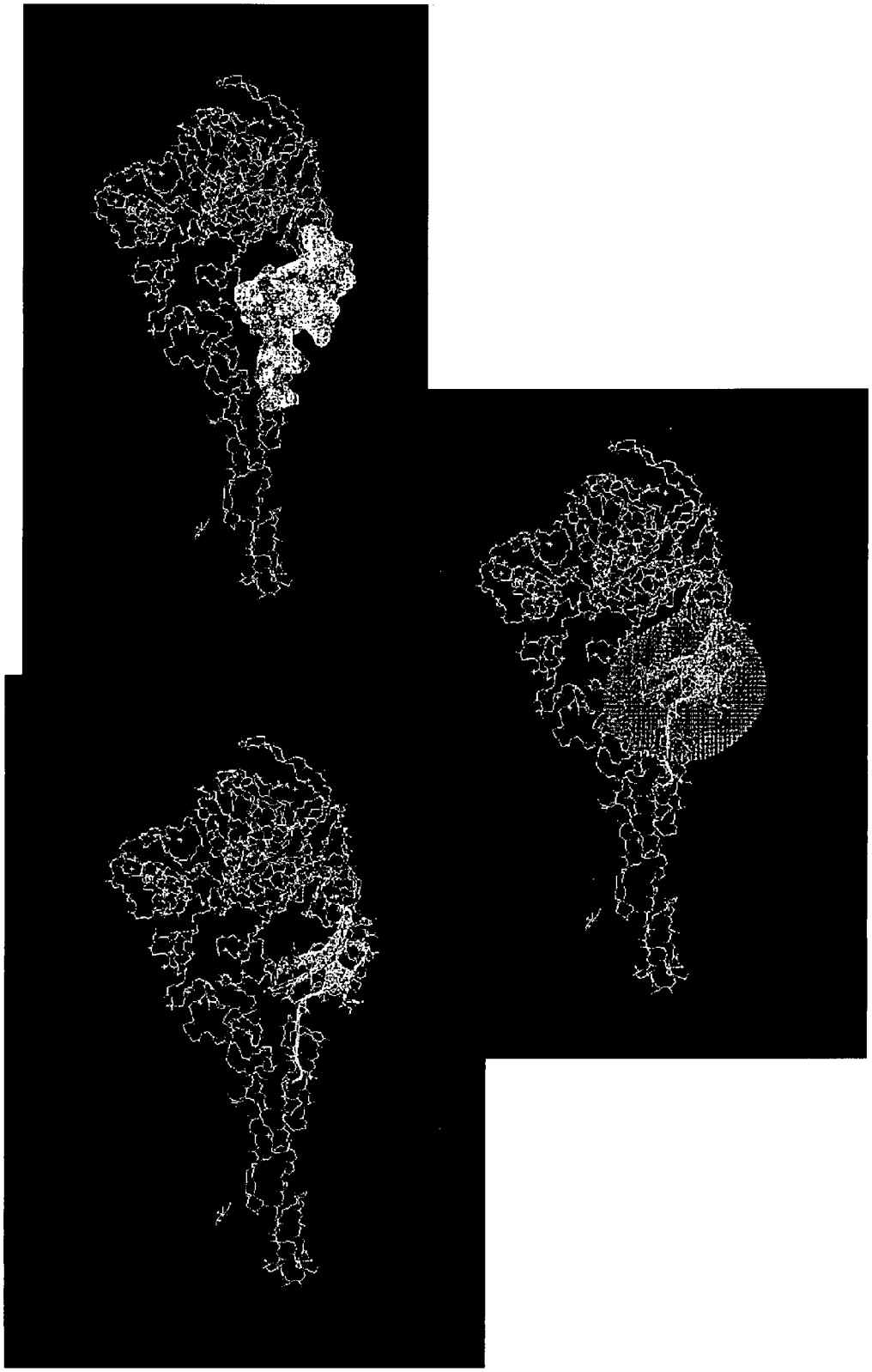

The present invention describes an osteogenic peptide or protein and compositions thereof for enhancing bone mineralization for bone regeneration or bone repair. It is also provided a method of screening for agents that alter the activity of NELL-1 peptide or protein or a gene that expresses NELL-1 peptide or protein.

DEFINITIONS

The term "antibody", as used herein, includes various forms of modified or altered antibodies, such as an intact immunoglobulin, an Fv fragment containing only the light and heavy chain variable regions, an Fv fragment linked by a disulfide bond (Brinkmann et al. (1993) Proc. Natl. Acad. Sci. USA, 90: 547-551), an Fab or (Fab)'2 fragment containing the variable regions and parts of the constant regions, a single-chain antibody and the like (Bird et al. (1988) Science 242: 424-426; Huston et al. (1988) Proc. Nat. Acad. Sci. USA 85: 5879-5883). The antibody can be of animal (especially mouse or rat) or human origin or can be chimeric (Morrison et al. (1984) Proc Nat. Acad. Sci. USA 81: 6851-6855) or humanized (Jones et al. (1986) Nature 321: 522-525, and published UK patent application #8707252).

The terms "binding partner", or "capture agent", or a member of a "binding pair" refers to molecules that specifically bind other molecules to form a binding complex such as antibody-antigen, lectin-carbohydrate, nucleic acid-nucleic acid, biotin-avidin, etc.

The terms "carrier," "pharmaceutically acceptable carrier," "delivery vehicle," or "vehicle" can be used interchangeably.

The term "specifically binds", as used herein, when referring to a biomolecule (e.g. protein, nucleic acid, antibody, etc.), refers to a binding reaction which is determinative of the presence biomolecule in heterogeneous population of molecules (e.g. proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The term osteoporosis refers to a heterogeneous group of disorders characterized by decreased bone mass and fractures. Clinically, osteoporosis is segregated into type I and type II. Type I osteoporosis occurs predominantly in middle aged women and is associated with estrogen loss at the menopause, while osteoporosis type II is associated with advancing age.

Osteogenesis imperfecta (OI) refers to a group of inherited connective tissue diseases characterized by bone and soft connective tissue fragility (Byers & Steiner (1992) Annu. Rev. Med. 43: 269-289; Prockop (1990) J. Biol. Chem. 265: 15349-15352). Males and females are affected equally, and the overall incidence is currently estimated to be 1 in 5,000-14,000 live births. Hearing loss, dentinogenesis imperfecta, respiratory insufficiency, severe scoliosis and emphysema are just some of the conditions that are associated with one or more types of OI. While accurate estimates of the health care costs are not available, the morbidity and mortality associated with OI certainly result from the extreme propensity to fracture (OI types I-IV) and the deformation of abnormal bone following fracture repair (OI types II-IV).

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that can have alternate backbones, comprising, for example, phosphoramide, phosphorothioate, phosphorodithioate, O-methylphosphoroamidite linkages, and peptide nucleic acid backbones and linkages. Other analog nucleic acids include those with positive backbones, non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids. Several nucleic acid analogs are described in Rawls, C & E News Jun. 2, 1997 page 35. These modifications of the ribose-phosphate backbone can be done to facilitate the addition of additional moieties such as labels, or to increase the stability and half-life of such molecules in physiological environments.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g. Tijssen (1993) Laboratory Techniques in Biochemistry and Molecular Biology—Hybridization with Nucleic Acid Probes part I, chapt 2, Overview of principles of hybridization and the strategy of nucleic acid probe assays, Elsevier, N.Y. (Tijssen). Generally, highly stringent hybridization and wash conditions are selected to be about 5° C. lower than the thermal melting point ($T_m$) for the specific sequence at a defined ionic strength and pH. $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g. Sambrook (1989) Molecular Cloning: A Laboratory Manual (2nd ed.) Vol. 1-3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g. Sambrook supra.) for a description of SSC buffer). Often, a high stringency wash is preceded by a low stringency wash to remove background probe signal. An example medium stringency wash for a duplex of, e.g. more than 100 nucleotides, is 1.times.SSC at 45° C. for 15 minutes. An example of a low stringency wash for a duplex of, e.g. more than 100 nucleotides, is 4× to 6×SSC at 40° C. for 15 minutes.

The term "osteogenic cells" refers to cells capable of mineralizing. Osteogenic cells include osteoblasts, osteoblast like cells, mesenchymal cells, fibroblast cells, fetal embryonic cells, stem cells, bone marrow cells, dura cells, chondrocytes, and chondroblastic cells.

The term "osteochondroprogenitor" refers to any cell capable of forming cartilage, e.g., less differentiated osteogenic cells which are capable of mineralizing and/or forming cartilage. Osteochondroprogenitor cells include osteoblasts, osteoblast like cells, mesenchymal cells, fibroblast cells, fetal embryonic cells, stem cells, bone marrow cells, dura cells, chrondrocytes, and chondroblastic cells.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g. proteins, nucleic acids, etc.). Preferred small organic molecules range in size up to about 5000 Daltons, more preferably up to 2000 Daltons, and most preferably up to about 1000 Daltons, about 500 Daltons, or about 200 Daltons.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "animal" refers to a mammal, which includes any warm-blooded vertebrate of the class Mammalia, whose females possess milk-secreting mammae for the nourishment of the young, which includes for example: human beings, horses, dogs, cats, rodents, cattle, whales, bats, etc. The term "protein structure" can refer to protein structure forms derived experimentally or through computer assisted software predictions. Common experimental methods used to determine a protein's structure are x-ray crystallography and nuclear magnetic resonance (NMR). In x-ray crystallography, scientists determine protein structure by measuring the directions and intensities of x-ray beams diffracted from high-quality crystals of a purified protein molecule. NMR uses high magnetic fields and radio-frequency pulses to manipulate the spin states of nuclei. The positions and intensities of the peaks on the resulting spectrum reflect the chemical environment and nucleic positions within the molecule.

In research that received the 1972 Nobel Prize in Chemistry, Christian Anfinsen showed that a completely unfolded protein could fold spontaneously to its biologically active state, indicating that a sequence of amino acids contains all of the information needed to specify its 3D structure. Thus, to those well versed in the art, it is possible to utilize computer programs that estimate the molecular forces between all of the protein's atoms and the surrounding molecules to develop algorithms that predict protein structure (for example of a general site, please refer to the website of San Diego Supercomputer Center for examples of algorithms) (for example of a specific NELL-1 site, please refer to the Database of Comparative Protein Structure Models maintained by the University of California, San Francisco, the website of SMART (Simple Modular Architecture Research Tool), or the website of ExPASy Proteomics Tools).

The term "domain" can refer to any discrete portion of the NELL-1 molecule that has an already defined function, an anticipated function, or a function to be defined in the future. FIGS. 2 and 3 show examples of anticipated NELL-1 domains with anticipated functions. For example, the observed strong binding interaction between recombinant Nell-1 and heparin sulfate may possibly be mediated by TSP-N (Kuroda, S., M. Oyasu, et al. (1999). "Biochemical characterization and expression analysis of neural thrombospondin-1-like proteins NELL-1 and NELL2." *Biochem Biophys Res Commun* 265(1): 79-86.). The TSP-N module in Nell-1 can potentially interact with cell surface heparin sulfate proteoglycans to mediate general cellular functions such as spreading, focal adhesion, disassembly, and endocytosis (Bornstein, P. (1995). "Diversity of function is inherent in matricellular proteins: an appraisal of thrombospondin 1." *J Cell Biol* 130(3): 503-6). Additionally, NELL-1 may be a member of the chordin-like CR domain family, which includes chordin, kielin, crossveinless, twisted gastrulation, and connective-tissue growth factor (Abreu, J. G., N. I. Ketpura, et al. (2002). "Connective-tissue growth factor (CTGF) modulates cell signaling by BMP and TGF-beta." *Nat Cell Biol* 4(8): 599-604). CR domains can mediate specific interactions with BMPs and other members of the TGF-β superfamily in either a pro- or anti-ligand fashion (Abreu, Ketpura et al. 2002). In addition, CR domains affect other functions such as receptor binding and trimer formation. However, it is conceivable that new domains could be identified in NELL-1 and FIGS. 2 and 3 are not meant to be limiting. Overall it is anticipated that NELL-1 will have specific domains that carry out specific functions such as protein secretion, ligand binding, trimer or tetramer formation etc.

The term "conformational change" refers to any change in NELL-1 protein structure as a result of microenvironmental interactions such as ionic interactions, hydrophobic/hydrophilic interactions, protein interactions, receptor interactions, cell-cell interactions, etc. For example, heparin sulfate binding to NELL-1 is known to induce a conformational change based on differential anti-NELL-1 antibody binding characteristics in the presence or absence of heparin sulfate.

The term "cartilage" refers to all forms of cartilage including, but not limited to, hyaline, elastic, and fibrocartilage.

The term proteoglycan can refer to various extracellular matrix molecules including heparin sulfate, heparan sulfate, dermatan sulfate, chondroitin sulfate.

The term glycosaminoglycan can refer to various extracellular matrix molecules including hyaluronic acid.

This invention provides pertains to the discovery that the NELL-1 gene product enhances tissue (e.g. bone) mineralization and cartilage formation. Without being bound to a particular theory, it is believed that the NELL-1 protein can execute its function by interacting with various proteins including members of the TGFβ superfamily and with other molecules present in the extracellular matrix such as glycosaminoglycan and heparin or heparan sulfate-like molecules to promote cell differentiation and thus enhance desired cell functions.

The term heparin and heparan sulphate refer to molecules that both have the same basic structure consisting of repeating disaccharides of GlcUA and GlcNAc. The size of an individual chain can reach 100 kDa, but normally they are below 50 kDa. Heparin is widely known for its anti-coagulant action, the one based on its binding with antithrombin III. Distinction between heparin and heparan sulphate is difficult, since both structural and functional criteria are inadequate to separate these two forms. They both contain numerous variations of sulphation and L-epimerization. N-deacetylation and the successive N-sulfation appear to be the critical steps, since the additional modifications locate mainly in the regions where N-sulfation has already occurred. The amount of N-sulfation has occasionally been used to make distinction between heparin and heparan sulphate so that in heparan sulphate the proportion of N-sulfation is below 50% (Fraansson, L. A., I. Carlstedt, et al. (1986). "The functions of the heparan sulphate proteoglycans." *Ciba Found Symp*, 124: 125-42), while in heparin it is usually 70% or higher (Roden, L., S. Ananth, et al. (1992). "Heparin—an introduction." *Adv Exp Med Biol*, 313: 1-20). Epimerization of the glucuronic acid and the successive 2-sulphation are typical for both glycosaminoglycans. Sulphation at position 2 of glucuronic acid seems to prevent the epimerization backwards to the form that is more favored energetically.

NELL-1 Peptide

NELL-1 peptide is an 810 amino acid peptide, distributed primarily in bone. (SEQ. ID NO:1) NELL-1 peptide is a trimeric peptide and has an amino acid sequence as reported by Ting (Ting et al., (1999) J Bone Mineral Res, 14:80-89; and GenBank Accession Number U57523) (FIGS. 2 and 3).

In some embodiments, a NELL-1 protein is a protein expressed by the NELL-1 gene or cDNA (SEQ ID NO: 2 or 7), which is disclosed by Watanabe et al. (1996) Genomics 38 (3): 273-276; Ting et al. (1999) J Bone Mineral Res, 14: 80-89; and GenBank Accession Number U57523), and includes SEQ ID NO: 1 or 8. The NELL-1 protein can include NELL-1 protein fragments that retain the ability to induce bone mineralization. The NELL-1 protein can be a native NELL-1 protein or a recombinant protein. The term "NELL-1" protein includes NELL-1 peptide, a fragment thereof, or a derivative thereof. The term NELL-1 protein also includes functional equivalents or conformational equivalents of NELL-1 peptide. Functional equivalents or conformational equivalents of NELL-1 can be derived by reference to functional domain structures or conformational structures of NELL-1. Some computer generated structures of NELL-1 are shown in FIGS. 4A-4D.

NELL-1 Related Agents

In some other embodiments, the term "NELL-1" peptide or protein can be a NELL-1 related agent, which can be a fragment of NELL-1 peptide, a derivative of NELL-1 peptide, a splice variant of NELL-1 peptide, or a structural, functional, or conformational equivalent of NELL-1 peptide.

Computer structural simulation of NELL-1 has been reported. The peptide is reported to have a structure as shown in FIGS. 4A-4D. Critical functional domains of NELL-1 include but are not limited to the regions shown in FIGS. 2, 3, and 4A-4D.

Accordingly, in one embodiment, the NELL-1 related agent can be a peptide or protein that has one or more function domains of NELL-1, as described above, or a functional equivalent of any of or a combination of these functional domains. In some embodiments, the functional domains can include mutated sequences and/or sequence knocked-outs provided that the domains function remain substantially unchanged.

In some embodiments, the NELL-1 related agent can be can be a peptide or polypeptide having an degree of homology of about 50%, about 55%, about 60%, about 65%, about 70%, about 75%, about 80%, about 85%, about 90%, about 95% or about 99% to a NELL-1 protein.

In some embodiments, the NELL-1 related agent can be a conformational equivalent of any or all the functional domains of NELL-1 peptide. Such conformational equivalent(s) can have an amino acid sequence similar to that of NELL, e.g., having a degree of homology of about 50%, about 55%, about 60%, about 65%, about 70%, about 75%, about 80%, about 85%, about 90%, about 95% or about 99% to NELL-1 protein. In some other embodiments, the conformational equivalent can have an amino acid sequence substantially different or unrelated to NELL-1 peptide, provided that such equivalent(s) have a 2D or 3D conformation substantially similar to the 2D or 3D conformation of any or all the functional domains of NELL-1 peptide or substantially similar to the 2D or 3D conformation of NELL-1 peptide, one of which is shown in FIG. 2. The 2D or 3D conformation can be, but not limited to, NELL-1 protein structure forms derived experimentally or through computer assisted soft ware predictions. Although not yet described for NELL-1, examples of a conformational equivalent can have substantially different amino acid sequences include the example of bone morphogenetic protein 7 and growth differentiation factor 5 (Schreuder et al. Crystal structure of recombinant human growth and differentiation factor 5: Evidence for interaction of the type I and type II receptor-binding sites. Biochemical and Biophysical Research Communications 329 (2005) 1076-1086).

In some embodiments, the NELL-1 related agent can be a compound whose primary protein structure is different from that of NELL-1 but has a final structure that is similar or the same as that of NELL-1.

In some further embodiments, the NELL-1 related agent also includes splice variants of NELL-1 peptide. Exons in the NELL-1 peptide can be knocked out so as to make splice variants of NELL-1 peptide. For example, NELL-1 can be spliced into two or three fragments forming the trimeric NELL-1 peptide by splicing NELL-1 along the two exon regions. Methods and procedures for making splice variants of a protein or peptide are well known in the art (see, U.S. application publication No. 20050148511, the teaching of which is incorporated herein by reference).

In some embodiments, the NELL-1 peptide described herein can be a derivative of the NELL-1 peptide. The term "derivative" as used herein, refers to any chemical or biological compounds or materials derived from a NELL-1 peptide, structural equivalents thereof, or conformational equivalents thereof. For example, such a derivative can include any pro-drug form, PEGylated form, or any other form of a NELL-1 peptide that renders the NELL-1 peptide more stable or to have a better osteo philicity or lipophilicity. In some embodiments, the derivative can be a NELL-1 peptide attached to poly(ethylene glycol), a poly(amino acid), a hydrocarbyl short chain having C1-C20 carbons, or a biocompatible polymer. In some embodiments, the term "derivative" can include a NELL-1 peptide mimetics. Synthesis of mimetics of a peptide is well document in the art. The following describes an example of the basic procedure for the synthesis of a peptide, including a peptide mimetics:

Before the peptide synthesis starts, the amine terminus of the amino acid (starting material) can protected with FMOC (9-fluoromethyl carbamate) or other protective groups, and a solid support such as a Merrifield resin (free amines) is used as an initiator. Then, step (1) through step (3) reactions are performed and repeated until the desired peptide is obtained: (1) a free-amine is reacted with carboxyl terminus using carbodiimide chemistry, (2) the amino acid sequence is purified, and (3) the protecting group, e.g., the FMOC protecting group, is removed under mildly acidic conditions to yield a free amine. The peptide can then be cleaved from the resin to yield a free standing peptide or peptide mimetics.

In some embodiments the peptide derivative described herein includes a physically or chemically modified NELL-1 peptide. Physically modified peptide can be modification by, for example, modification by ionic force such as forming an ionic pair with a counterion, modification by hydrogen bonding, modification by modulation of pH, modulation by solvent selection, or modification by using different protein folding/unfolding procedures, which can involve selection of folding/unfolding temperature, pH, solvent, and duration at different stage of folding/unfolding.

In some embodiments, the peptide derivative can include a chemically modified NELL-1 peptide. For example, a short hydrocarbon group(s) (e.g. methyl or ethyl) can be selectively attached to one or multiple sites on the NELL-1 peptide molecule to modify the chemical and/or physical properties of the peptide. In some embodiments, a mono-, oligo- or poly(ethylene glycol) (PEG) group(s) can be selectively attached to one or multiple sites on the NELL-1 peptide molecule to modify the chemical and/or physical properties of the peptide by commonly known protein PEGylation procedures (see, e.g., Mok, H., et al., Mol. Ther., 11(1):66-79 (2005)).

V. Increasing Bone Mineralization Using NELL-1 Nucleic Acids and/or Polypeptides.

In still another embodiment, this invention provides methods and compositions to enhance bone growth. This is useful in a variety of contexts including, but are not limited to, bone reconstruction, such as is used to reconstruct defects occurring as a result of trauma, cancer surgery or errors in development, the treatment of osteogenesis imperfecta, the treatment of osteoporosis, and the healing of major or minor bone fractures.

In some embodiments, in a manner analogous to the use of bone morphogenic proteins (e.g. BMP-1 through BMP-24), the NELL-1 polypeptide(s) can be used to speed repair of bone fractures or to induce bone repair or replacement under circumstances where natural healing is limited or non-existent. In generally such methods involve increasing the amount of a NELL-1 gene product at or near the fracture site in a bone. The NELL-1 gene product concentration can be increased by one or more of a number of methods. In one approach, cells at or near the bone fracture site are induced to express elevated levels of NELL-1. This is accomplished, for example, by the use of modulators of NELL-1 expression, by altering the NELL-1 promoter, or by transfecting the cell with a construct that expresses NELL-1. This can be accomplished in vivo, or, in another embodiment, such cells can be modified to overexpress NELL-1 ex vivo and then introduced back into the subject organism (e.g. at or near a fracture site).

Cells expressing or overexpressing NELL-1 can be incorporated into bone graft materials and/or NELL-1 polypeptides can be incorporated into such bone graft materials. These graft materials can be used in the treatment of fractures or to facilitate the replacement/healing of prostheses or bone transplants.

The methods generally involve increasing NELL-1 protein concentration at or near a bone or at or in a bone progenitor cell and/or contacting a cell (e.g. a bone progenitor cell) with a NELL-1 polypeptide or with a vector encoding a NELL-1 polypeptide. This can be accomplished by transforming a bone precursor cell so that it expresses elevated levels of endogenous NELL-1 or so that it expresses NELL-1 from an exogenous transfected NELL-1 nucleic acid, or by contacting the bone, bone fracture site, bone precursor cells with NELL-1 protein(s) or local or systemic administration of a NELL-1 protein.

As used herein, the term "bone progenitor cells" refers to any or all of those cells that have the capacity to ultimately form, or contribute to the formation of, new bone tissue. This includes various cells in different stages of differentiation, such as, for example, stem cells, bone marrow cells, fibroblasts, vascular cells, osteoblasts, chondroblasts, osteoclasts, and the like. Bone progenitor cells also include cells that have been isolated and manipulated in vitro, e.g. subjected to stimulation with agents such as cytokines or growth factors or even genetically engineered cells. The particular type or types of bone progenitor cells that are stimulated using the methods and compositions of the invention are not important, so long as the cells are stimulated in such a way that they are activated and, in the context of in vivo embodiments, ultimately give rise to new bone tissue.

Stem cells and bone marrow cells can be differentiated into bone cells or bone progenitor cells under various defined in vitro conditions or incompletely defined in vivo conditions. For in vivo example, bone marrow cells can be obtained from a mammal by simple needle aspiration. At this point, Nell-1 protein can be directly applied to the cells and the cell/protein mixture (plus or minus an additional carrier/scaffold construct) can be immediately implanted or injected. Alternatively, the isolated bone marrow cells can first be cultured to remove hematoppoietic cells and then treated with Nell-1 before implantation or injection. For instance, The cells were centrifuged and suspended in Dulbecco's Modified Eagles's Medium (DMEM) (Gibco BRL, Grand Island, N.Y.) containing 10% fetal bovine serum (FBS) (Hyclone, Logan, Utah), 100 U/mL penicillin, 100 µg/mL streptomycin, and 2 mmol/L L-glutamine (Sigma, St. Louis, Mo.). Hematopoietic cells, which did not adhere to flasks, were discarded, and the cells which adhered represented a population of primary BMSCs. After the first passage, cells were cultured in DMEM medium supplemented with 50 µg/mL ascorbic acid, 10 mmol/L β-glycerophosphate, and 10-8 mol/L dexamethasone until utilized for experiments. Experiments were performed with cells from the second passage.

The term "bone progenitor cell" is also used to particularly refer to those cells that are located within, are in contact with, or migrate towards (i.e., "home to"), bone progenitor tissue and which cells directly or indirectly stimulate the formation of mature bone. As such, the progenitor cells can be cells that ultimately differentiate into mature bone cells themselves, i.e., cells that "directly" form new bone tissue. Cells that, upon stimulation, attract further progenitor cells or promote nearby cells to differentiate into bone-forming cells (e.g. into osteoblasts, osteocytes and/or osteoclasts) are also considered to be progenitor cells in the context of this disclosure—as their stimulation "indirectly" leads to bone repair or regeneration. Cells affecting bone formation indirectly can do so by the elaboration of various growth factors or cytokines, or by their physical interaction with other cell types. The direct or indirect mechanisms by which progenitor cells stimulate bone repair is not necessary a consideration in practicing this invention. Bone progenitor cells and bone progenitor tissues can be cells and tissues that, in their natural environment, arrive at an area of active bone growth, repair or regeneration. In terms of bone progenitor cells, these can also be cells that are attracted or recruited to such an area. These can be cells that are present within an artificially-created osteotomy site in an animal model. Bone progenitor cells can also be isolated from animal or human tissues and maintained in an in vitro environment. Suitable areas of the body from which to obtain bone progenitor cells are areas such as the bone tissue and fluid surrounding a fracture or other skeletal defect (whether or not this is an artificially created site), or indeed, from the bone marrow. Isolated cells can be stimulated using the methods and compositions disclosed herein and, if desired, be returned to an appropriate site in an animal where bone repair is to be stimulated. In such cases, the nucleic-acid containing cells would themselves be a form of therapeutic agent. Such ex vivo protocols are well known to those of skill in the art. In preferred embodiments of the invention, the bone progenitor cells and tissues will be those cells and tissues that arrive at the area of bone fracture or damage that one desires to treat. Accordingly, in treatment embodiments, there is no difficulty associated with the identification of suitable target progenitor cells to which the present therapeutic compositions should be applied. It is sufficient in such cases to obtain an appropriate stimulatory composition (e.g. a NELL-1 polypeptide), as disclosed herein, and contact the site of the bone fracture or defect with the composition. The nature of this biological environment is such that the appropriate cells will become activated in the absence of any further targeting or cellular identification by the practitioner.

A) Transformation of Cells to Increase NELL-1 Production.

In a more preferred embodiment, the NELL-1 gene expressing nucleic acids (e.g. cDNA(s)) can be cloned into gene therapy vectors that are competent to transfect cells (such as human or other mammalian cells) in vitro and/or in vivo. The methods and procedures of such cloning and cell transfection are described in U.S. application Ser. No. 09/412, 297, filed on Oct. 5, 1999, the teachings of which are incorporated herein in their entirety by reference.

B) Administration of Exogenously Produced NELL-1

1) Delivery of NELL-1 Proteins to Target Cells.

The NELL-1 proteins or related agents of this invention are useful for promoting cellular differentiation. To promote cell differentiation, NELL-1 proteins or related agents are useful for intravenous, parenteral, topical, oral, or local administration (e.g. by aerosol or transdermally). Particularly preferred modes of administration include intraarterial injection, injection into fracture sites or delivery in a biodegradable matrix. The NELL-1 proteins agents can be combined with a pharmaceutically acceptable carrier, which can be referred to as carrier or excipient, to form a pharmacological composition.

In some embodiments, the carrier can include a chemical gel that includes primary bonds formed due to changes in pH, ionic environment, and solvent concentration. Examples of such chemical gels can be, but are not limited to, polysaccharides such as chitosan, chitosan plus ionic salts such as beta-glycerophosphates, aginates plus Ba2+, Sr 2+, Ca2+, Mg2+, collagen, fibrin, plasma or combinations thereof.

In some embodiments, the carrier can include a physical gel that include secondary bonds formed due to temperature changes. Examples of such physical gels can be, but are not limited to, alginate, poly(ethylene glycol)-poly(lactic acid-co-glycolic acid)-poly(ethylene glycol) (PEG-PLGA-PEG) tri-block copolymers, agarose, and celluloses. In some embodiments, physical gels that can be used in the composition described herein can include physical gels that are liquid under high shear but gels to solid at low shear. Examples of such physical gels include, but are not limited to, hyaluronic acid, or polyethylene oxides. The physical gels can have pre-formed materials with pre-defined dimensions and shape.

In some embodiments, the carrier described herein can include a material that degrade or release active agents in response to a stimulus. Some examples of such stimuli are mechanical stimuli, light, temperature changes, pH changes, change of ionic strength, or electromagnetic field. Such materials are know in the art. some examples of such materials are chitosan, alginates, pluronics, methyl cellulose, hyaluronic acids, and polyethylene oxides. Other examples are described by Brandl F, Sommer F, Goepferich A. "Rational design of hydrogels for tissue engineering: Impact of physical factors on cell behavior" in Biomaterials. Epub 2006 Sep. 29.

In some embodiments, the carrier can include a gel containing any of hydroxyapatites, apatites, tricalcium phostphates, calcium phosphates, bioactive glass, human allograft bone and cartilage, bovine bone and cartilage, or their mixtures thereof.

In some embodiments, the carrier including any of the gels described above can further include a crosslinker to further tailor degradation kinetics and controlled release. Alternatively, in some embodiments, the carrier can include an interpenetrating phase composite or interpenetrating network (IPN) that includes any of the above described gels. Some examples of the crosslinker includes, but are not limited to, common crosslinking agents (polyalkylene oxide, ethylene dimethacrylate, N,N'-methylenebisacrylamide, methylenebis(4-phenyl isocyanate), ethylene dimethacrylate, divinylbenzene, allyl methacrylate, carbodiimidazole, sulfonyl chloride, chlorocarbonates, n-hydroxysuccinimide ester, succinimidyl ester, epoxides, aryl halides, sulfasuccinimidyl esters, and maleimides); PEG based crosslinkers (e.g. MAL-dPEGx-NHS-esters, MAL-dPEGx acid, Bis-MAL-dPEGx, etc.) and photo/light activated crosslinkers, N-hydroxysuccinimide-based crosslinkers, dilysine, trilysine, and tetralysine.

In some embodiments, the carrier can be a polymeric carrier or non-polymeric carrier. In some embodiments, the carrier can be biodegradable, such as degradable by enzymatic or hydrolytic mechanisms. Examples of carriers include, but are not limited to synthetic absorbable polymers such as such as but not limited to poly($\alpha$-hydroxy acids) such as poly (L-lactide) (PLLA), poly (D, L-lactide) (PDLLA), polyglycolide (PGA), poly (lactide-co-glycolide (PLGA), poly (-caprolactone), poly (trimethylene carbonate), poly (p-dioxanone), poly (-caprolactone-co-glycolide), poly (glycolide-co-trimethylene carbonate) poly (D, L-lactide-co-trimethylene carbonate), polyarylates, polyhydroxybutyrate (PHB), polyanhydrides, poly (anhydride-co-imide), propylene-co-fumarates, polylactones, polyesters, polycarbonates, polyanionic polymers, polyanhydrides, polyester-amides, poly(amino-acids), homopolypeptides, poly(phosphazenes), poly (glaxanone), polysaccharides, and poly(orthoesters), polyglactin, polyglactic acid, polyaldonic acid, polyacrylic acids, polyalkanoates; copolymers and admixtures thereof, and any derivatives and modifications. See for example, U.S. Pat. No. 4,563,489, and PCT Int. Appl. No. WO/03024316, herein incorporated by reference. Other examples of carriers include cellulosic polymers such as, but not limited to alkylcellulose, hydroxyalkylcellulose, methylcellulose, ethylcellulose, hydroxyethylcellulose, hydroxypropylcellulose, hydroxypropyl-methylcellulose, carboxymethylcellulose, and their cationic salts. Other examples of carriers include synthetic and natural bioceramics such as, but not limited to calcium carbonates, calcium phosphates, apatites, bioactive glass materials, and coral-derived apatites. See for example U.S. Patent Application 2002187104; PCT Int. Appl. WO/9731661; and PCT Int. Appl. WO/0071083, herein incorporated by reference.

In one embodiment, the carrier can further be coated by compositions, including bioglass and or apatites derived from sol-gel techniques, or from immersion techniques such as, but not limited to simulated body fluids with calcium and phosphate concentrations ranging from about 1.5 to 7-fold the natural serum concentration and adjusted by various means to solutions with pH range of about 2.8-7.8 at temperature from about 15-65° C. (see, for example, U.S. Pat. Nos. 6,426,114 and 6,013,591; and PCT Int. Appl. WO/9117965, which are herein incorporated by reference).

Other examples of carriers include, collagen (e.g. Collastat, Helistat collagen sponges), hyaluronan, fibrin, chitosan, alginate, and gelatin. See for example, PCT Int. Appls. WO/9505846; WO/02085422, which are herein incorporated by reference.

In one embodiment, the carrier can include heparin-binding agents; including but not limited to heparin-like polymers e.g. dextran sulfate, chondroitin sulfate, heparin sulfate, fucan, alginate, or their derivatives; and peptide fragments with amino acid modifications to increase heparin affinity (see for example, Journal of Biological Chemistry (2003), 278(44), p. 43229-43235, which are herein incorporated by reference).

In one embodiment, the composition can be in the form of a liquid, solid or gel.

In one embodiment, the substrate can include a carrier that is in the form of a flowable gel. The gel can be selected so as to be injectable, such as via a syringe at the site where cartilage formation is desired. The gel can be a chemical gel which can be a chemical gel formed by primary bonds, and controlled by pH, ionic groups, and/or solvent concentration. The gel can also be a physical gel which can be formed by secondary bonds and controlled by temperature and viscosity. Examples of gels include, but are not limited to, pluronics, gelatin, hyaluronan, collagen, polylactide-polyethylene glycol solutions and conjugates, chitosan, chitosan & b-glycerophosphate (BST-gel), alginates, agarose, hydroxypropyl cellulose, methyl cellulose, polyethylene oxide, polylactides/glycolides in N-methyl-2-pyrrolidone. See for example, Anatomical Record (2001), 263(4), 342-349, herein incorporated by reference.

In one embodiment, the carrier can be photopolymerizable, such as by electromagnetic radiation with wavelength of at least about 250 nm. Example of photopolymerizable polymers include polyethylene (PEG) acrylate derivatives, PEG methacrylate derivatives, propylene fumarate-co-ethylene glycol, polyvinyl alcohol derivatives, PEG-co-poly(-hydroxy acid) diacrylate macromers, and modified polysaccharides such as hyaluronic acid derivatives and dextran methacrylate.

See for example, U.S. Pat. No. 5,410,016, herein incorporated by reference.

In one embodiment, the substrate can include a carrier that is temperature sensitive. Examples include carriers made from N-isopropylacrylamide (NiPAM), or modified NiPAM with lowered lower critical solution temperature (LCST) and enhanced peptide (e.g. NELL1) binding by incorporation of ethyl methacrylate and N-acryloxysuccinimide; or alkyl methacrylates such as butylmethacrylate, hexylmethacrylate and dodecylmethacrylate. PCT Int. Appl. WO/2001070288; U.S. Pat. No. 5,124,151 herein incorporated by reference.

In one embodiment, where the carrier can have a surface that is decorated and/or immobilized with cell adhesion molecules, adhesion peptides, and adhesion peptide analogs which can promote cell-matrix attachment via receptor mediated mechanisms, and/or molecular moieties which can promote adhesion via non-receptor mediated mechanisms binding such as, but not limited to polycationic polyamino-acid-peptides (e.g. poly-lysine), polyanionic polyamino-acid-peptides, Mefp-class adhesive molecules and other DOPA-rich peptides (e.g. poly-lysine-DOPA), polysaccharides, and proteoglycans. See for example, PCT Int. Appl. WO/2004005421; WO/2003008376; WO/9734016, herein incorporated by reference.

In one embodiment, the carrier can include various naturally occurring matrices or their components such as devitalized cartilage matrix, demineralized bone matrix, or other components derived from allograft, xenograft, or any other naturally occurring material derived from Monera, Protista, Fungi, Plantae, or Animalia kingdoms.

In one embodiment, the carrier can include comprised of sequestering agents such as, but not limited to, collagen, gelatin, hyaluronic acid, alginate, poly(ethylene glycol), alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, blood, fibrin, polyoxyethylene oxide, calcium sulfate hemihydrate, apatites, carboxyvinyl polymer, and poly(vinyl alcohol). See for example, U.S. Pat. No. 6,620,406, herein incorporated by reference.

In one embodiment, the carrier can include surfactants to promote NELL-1 stability and/or distribution within the carrier materials such as, but not limited to polyoxyester (e.g. polysorbate 80, polysorbate 20 or Pluronic F-68).

In one embodiment, the carrier can include buffering agents such as, but not limited to glycine, glutamic acid hydrochloride, sodium chloride, guanidine, heparin, glutamic acid hydrochloride, acetic acid, succinic acid, polysorbate, dextran sulfate, sucrose, and amino acids. See for example, U.S. Pat. No. 5,385,887, herein incorporated by reference. In one embodiment, the carrier can include a combination of materials such as those listed above. By way of example, the carrier can a be PLGA/collagen carrier membrane. The membrane can be soaked in a solution including NELL-1 peptide.

In one embodiment, an implant for use in the human body can include a substrate including NELL-1 in an amount sufficient to induce cartilage formation or repair proximate to the implant.

In one embodiment, an implant for use in the human body can include a substrate having a surface including NELL-1 in an amount sufficient to induce cartilage formation or repair proximate to the implant.

In one embodiment, an implant for use in the human body can include a substrate having a surface including chondrogenic cells, and NELL-1 in an amount sufficient to induce cartilage formation or repair. In one embodiment, the implant can be seeded with cells, including but not limited to autologous cells, chondrogenic or osteoblastic cells, cells expressing NELL-1 or another chondrogenic molecule.

An implant can include a substrate formed into the shape of a mesh, pin, screw, plate, or prosthetic joint. By way of example, a substrate can be in a form of a dental or orthopedic implant, and NELL-1 can be used to enhance integration in bone in proximity to the implant. An implant can include a substrate that is resorbable, such as a substrate including collagen.

The NELL-1 peptide can be combined with a acceptable carrier to form a pharmacological composition. Acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a carrier, including a physiologically acceptable compound depends, for example, on the route of administration.

The compositions can be administered in a variety of unit dosage forms depending upon the method of administration. For example, unit dosage forms suitable can include powder, or injectable or moldable pastes or suspension.

The compositions of this invention can comprise a solution of the NELL-1 peptide dissolved in a pharmaceutically acceptable carrier, such as an aqueous carrier for water-soluble peptides. A variety of carriers can be used, e.g., buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of NELL-1 peptide in these formulations can vary widely, and will be selected primarily based on fluid volumes, viscosities, body weight and the like in accordance with the particular mode of administration selected and the patient's needs.

The dosage regimen will be determined by the clinical indication being addressed, as well as by various patient variables (e.g. weight, age, sex) and clinical presentation (e.g. extent of injury, site of injury, etc.).

However, a therapeutically effective dose of a NELL-1 peptide or agent useful in this invention is one which has a positive clinical effect on a patient or desired effect in cells as measured by the ability of the agent to enhance chondrogenic differentiation, as described above. The therapeutically effective dose of each peptide or agent can be modulated to achieve the desired clinical effect, while minimizing negative side effects. The dosage of the peptide or agent can be selected for an individual patient depending upon the route of administration, severity of the disease, age and weight of the patient, other medications the patient is taking and other factors normally considered by an attending physician, when determining an individual regimen and dose level appropriate for a particular patient.

In some instances cell differentiation may be guided by the carrier and accelerated by NELL-1.

Pharmaceutically acceptable carriers can contain a physiologically acceptable compound that acts, for example, to stabilize the composition or to increase or decrease the absorption of the agent. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the anti-mitotic agents, or excipients or other stabilizers and/or buffers.

Other physiologically acceptable compounds include wetting agents, emulsifying agents, dispersing agents or preservatives which are particularly useful for preventing the growth or action of microorganisms. Various preservatives are well known and include, for example, phenol and ascorbic acid. One skilled in the art would appreciate that the choice of a pharmaceutically acceptable carrier, including a physiologically acceptable compound depends, for example, on the rout of administration of the anti-mitotic agent and on the particular physio-chemical characteristics of the anti-mitotic agent. Preferred formulations for the delivery of bone morphogenic proteins (BMPs) are described in detail in U.S. Pat. No. 5,385,887.

The pharmaceutical compositions can be administered in a variety of unit dosage forms depending upon the method of administration. For example, unit dosage forms suitable for oral administration include powder, tablets, pills, capsules and lozenges. It is recognized that the NELL-1 protein(s), if administered orally, must be protected from digestion. This is typically accomplished either by complexing the protein with a composition to render it resistant to acidic and enzymatic hydrolysis or by packaging the protein in an appropriately resistant carrier such as a liposome. Means of protecting compounds from digestion are well known in the art (see, e.g. U.S. Pat. No. 5,391,377 describing lipid compositions for oral delivery of therapeutic agents).

The pharmaceutical compositions of this invention are particularly useful for topical administration e.g. in surgical wounds to treat facilitate bone reconstruction and/or repair. In another embodiment, the compositions are useful for parenteral administration, such as intravenous administration or administration into a body cavity or lumen of an organ. The compositions for administration will commonly comprise a solution of the NELL-1 protein dissolved in a pharmaceutically acceptable carrier, preferably an aqueous carrier for water-soluble proteins. A variety of carriers can be used, e.g. buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of NELL-1 protein in these formulations can vary widely, and will be selected primarily based on fluid volumes, viscosities, body weight and the like in accordance with the particular mode of administration selected and the patient's needs. Typically the NELL-1 proteins are utilized in the form of a pharmaceutically acceptable solution (including reconstitution from a lyophilized form). For example, the Nell-1 protein can be solubilized at concentrations of at least about 1 mg/ml, preferably about 2 to 8 mg/ml, so that a pharmaceutically effective amount of protein can be delivered without undue volumes of carrier being necessary. For some applications, concentrations above 2 mg/ml can be desirable.

The dosage regimen will be determined by the clinical indication being addressed, as well as by various patient variables (e.g. weight, age, sex) and clinical presentation (e.g. extent of injury, site of injury, etc.). In general, dosages of NELL peptides and other agents can be determined according to methods known in the art based on type of agent, the disease, and other factors such as age and gender.

In one embodiment, the dosage of NELL peptide generally ranges from 0.001 pg/mm$^2$ to 1 pg/mm$^2$, or more preferably from 0.001 ng/mm$^2$ to 1 ng/mm$^2$, or more preferably from 0.001 µg/mm$^2$ to 1 µg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage of NELL peptide generally ranges from 0.001 pg/ml to 1 pg/ml, or more preferably from 0.001 ng/ml to 1 ng/ml, or more preferably from 0.001 µg/ml to 1 µg/ml, or more preferably from 0.001 mg/ml to 1 mg/ml, or more preferably from 0.001 g/ml to 100 g/ml, with or without a particular carrier or scaffold. In yet another embodiment, the dosage of NELL peptide generally ranges from 0.001 pg/kg to 1 pg/kg, or more preferably from 0.001 ng/kg to 1 ng/kg, or more preferably from 0.001 µg/kg to 1 µg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

However, because NELL peptides can have effects on in vitro osteoblast apoptosis (Zhang, X., et al., J Bone Miner Res, 2003. 18(12): p. 2126-34), NELL dosages (e.g., NELL-1 dosages) that are significantly above an optimal range can not increase cartilage formation or repair. Accordingly, even more preferable dosages of NELL peptide shall not be significantly above the optimal dosage range. The even more preferable optimal dosage ranges of NELL peptides can vary according to factors such as the type, the age, the location, and the gender of a mammalian subject; the carrier or scaffold material employed; and the purity and potency of different NELL peptides. In one embodiment, the even more preferable optimal dosage ranges of NELL peptides includes but are not limited to 1 ng/mm$^2$ to 100 ng/mm$^2$, or even more preferably from 100 ng/mm$^2$ to 1000 ng/mm$^2$, or even more preferably from 1 µg/mm$^2$ to 100 µg/mm$^2$, or even more preferably from 100 µg/mm$^2$ to 1000 µg/mm$^2$. In another embodiment, the even more preferable optimal dosage ranges of NELL peptides includes but are not limited to 1 ng/ml to 100 ng/ml, or even more preferably from 100 ng/ml to 1000 ng/ml, or even more preferably from 1 µg/ml to 100 µg/ml, or even more preferably from 100 µg/ml to 1000 µg/ml. In yet another embodiment, even more preferable optimal dosage ranges of NELL peptide generally ranges from 1 µg/kg to 100 µg/kg, or even more preferably from 100 µg/kg to 1000 µg/kg, or even more preferably from 1 mg/kg to 100 mg/kg with or without a particular carrier or scaffold. Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth. As used herein, the term "significantly above the optimal range" means, e.g., about 1% to about 50%, about 5% to about 50%, about 10% to about 50%, about 20% to about 50%, about 30% to about 50%, or about 40% to 50% over the optimal range.

The dosage for inhibitors of NELL peptides varies according to the type of the inhibitor, the bone or cartilage condition to be treated, prevented, or ameliorated, and the age, the location, and the gender of the mammalian subject receiving the composition containing the inhibitor. Generally, the dosage for inhibitors of NELL peptides ranges from but at not limited to: 0.001 pg/mm$^2$ to 1 pg/mm$^2$, or more preferably from 0.001 ng/mm$^2$ to 1 ng/mm$^2$, or more preferably from 0.001 µg/mm$^2$ to 1 µg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage for inhibitors of NELL peptides generally ranges from 0.001 pg/ml to 1 pg/ml, or more preferably from 0.001 ng/ml to 1 ng/ml, or more preferably from 0.001 µg/ml to 1 µg/ml, or more preferably from 0.001 mg/ml to 1 mg/ml, or more preferably from 0.001 g/ml to 100 g/ml, with or without a particular carrier or scaffold. In yet another embodiment, the dosage for inhibitors of NELL peptides generally ranges from 0.001 pg/kg to 1 pg/kg, or more preferably from 0.001 ng/kg to 1 ng/kg, or more preferably from 0.001 µg/kg to 1 µg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

The dosage for modulators of receptors of NELL peptides varies according to the type of the inhibitor, the type of receptor, the bone or cartilage condition to be treated, prevented, or ameliorated, and the age, the location, and the gender of the mammalian subject receiving the composition containing the modulators of receptors of NELL peptides. Generally, the dosage for modulators of receptors of NELL peptides ranges from but at not limited to: 0.001 pg/mm$^2$ to 1 pg/mm$^2$, or more preferably from 0.001 ng/mm$^2$ to 1 ng/mm$^2$, or more preferably from 0.001 µg/mm$^2$ to 1 µg/mm$^2$, or more preferably from 0.001 mg/mm$^2$ to 1 mg/mm$^2$, or more preferably from 0.001 g/mm$^2$ to 1 g/mm$^2$, with or without a particular carrier or scaffold. In another embodiment, the dosage for modulators of receptors of NELL peptides generally ranges from 0.001 pg/ml to 1 pg/ml, or more preferably from 0.001 ng/ml to 1 ng/ml, or more preferably from 0.001 µg/ml to 1 µg/ml, or more preferably from 0.001 mg/ml to 1 mg/ml, or more preferably from 0.001 g/ml to 100 g/ml, with or without a particular carrier or scaffold. In yet another embodiment, the dosage for modulators of receptors of NELL peptides generally ranges from 0.001 pg/kg to 1 pg/kg, or more preferably from 0.001 ng/kg to 1 ng/kg, or more preferably from 0.001 µg/kg to 1 µg/kg, or more preferably from 0.001 mg/kg to 1 mg/kg, or more preferably from 0.001 gm/kg to 1 gm/kg, more preferably from 0.001 kg/kg to 1 kg/kg with or without a particular carrier or scaffold. Furthermore, it is understood that all dosages can be continuously given or divided into dosages given per a given timeframe. Examples of timeframes include but are not limited to every 1 hour, 2 hour, 4 hour, 6 hour, 8 hour, 12 hour, 24 hour, 48 hour, or 72 hour, or every week, 2 weeks, 4 weeks, or every month, 2 months, 4 months, and so forth.

2) Bone Graft Materials.

Bone wounds, as well as many other wound models, initiate a release of biologically active agents critical to the wound healing process. Bone morphogenic proteins (BMP), which naturally occur in bone, once released from the wound, stimulate osteoinduction and regenerate lost or damaged bone tissue. These same proteins, in a purified form, can be used to stimulate bone growth into a biodegradable matrix allowing for artificial creation of bone both within and external to the normal skeletal boundaries. Without being bound to a particular theory, it is believed that NELL-1 proteins can be used to stimulate bone re-mineralization in a manner analogous to the use of bone morphogenic proteins.

NELL-1 proteins can be administered systemically as discussed above. In addition, or alternatively, the NELL-1 protein can be applied directly to a bone or bone fracture site. This can be accomplished during surgery (e.g. when setting complex fractures, when reconstructing bone, when performing bone transplants, etc.) or can be accomplished by direct injection.

In certain preferred embodiments, particularly where bone reconstruction or repair is performed surgically, it is desired to administer the NELL-1 protein using a sustained delivery "vehicle". Sustained delivery vehicles include, but are not limited to biodegradable delivery vehicles. Preferred biodegradable delivery vehicles are preferably porous.

Much work has been done in developing biodegradable porous delivery vehicles for the controlled release of substances while also providing a location for cellular attachment and guided tissue regeneration. Biodegradable materials often separated into two categories: 1) those which are hydrophilic; and 2) those which are hydrophobic. Hydrophilic materials (demineralized freeze dried bone, ceramic, fibrin, gelatin, etc.) possess a high affinity for water which provides for easy incorporation of aqueous NELL-1 protein solutions within the internal porosity of the material. Hydrophobic materials (L-polylactic acid, D,L-polylactic acid, poly-glycolic acid, etc.), while potentially limitless in their range of porosities, gross size, shape and mechanical characteristics are more difficult to "infiltrate" with aqueous solutions. To increase deposition of solutions into internal surfaces of such materials, hydrophobic materials are often impregnated with the protein or a surfactant is used to facilitate impregnation with the protein (e.g. NELL-1).

Detailed descriptions of various biodegradable delivery materials comprising materials such as fibrinogen, polylactic acid (PLA), copolymer of lactic acid, polyhydroxyacids such as poly(3-hydroxybutyrate), porous ceramics, gelatin, agar, and the like, can be found, e.g. in U.S. Pat. Nos. 5,736,160, 4,181,983, 4,186,448, 3,902,497, 4,442,655, 4,563,489, 4,596,574, 4,609,551, 4,620,327, and 5,041,138, the teachings of which are incorporated herein by reference.

In some embodiments, the delivery vehicle can be the same as the carrier described above.

Other delivery vehicles include, but are not limited to bone graft materials. Bone graft materials can be derived from natural materials (e.g. transplanted bone or bone fragments), synthetic materials (e.g. various polymers and/or ceramics) or combinations of both. Bone graft materials are typically utilized to fill voids or otherwise replace lost bone material. Such graft materials are also often provided as components of prosthetic devices (e.g. bone replacements or supports) to facilitate tight bonding/annealing of the prosthetic with the living bone.

Bone grafts using bioactive glasses and calcium phosphates, collagen, mixtures and the like have good biocompatibility and give rise to bone tissue formation and incorporation in some cases. A number of different glasses, glass-ceramics, and crystalline phase materials have been used, either alone or in combination with acrylic polymerizable species, and other families of polymers, for restorative purposes. These include hydroxyapatite, fluorapatite, oxyapatite, Wollastonite, anorthite, calcium fluoride, agrellite, devitrite, canasite, phlogopite, monetite, brushite, octocalcium phosphate, Whitlockite, tetracalcium phosphate, cordierite, and Berlinite. Representative patents describing such uses include U.S. Pat. Nos. 3,981,736, 4,652,534, 4,643,982, 4,775,646, 5,236,458, 2,920,971, 5,336,642, and 2,920,971. Additional references include Japanese Patent No. 87-010939 and German Patent OS 2,208,236. Other references can be found in W. F. Brown, "Solubilities of Phosphate & Other Sparingly Soluble Compounds," Environmental Phosphorous Handbook, Ch. 10 (1973). In addition to the foregoing, certain animal derived materials, including coral and nacre, have also been used in biomaterials for restorative purposes.

The bone graft can include between about 0.001% to 10% of NELL-1 peptide or a related agent. In some embodiments, the bone graft can include NELL-1 in an amount to provide for a dosage described above.

Other bone graft materials include a pliable, moldable acrylic-based bone cement reinforced with from 15 to 75% by weight of a bioactive glass together with between 1 and 10% by weight of vitreous mineral fibers (U.S. Pat. No. 4,239,113), bone fillers such as tricalcium phosphate and bioceramic $A_2$ into bisphenol-A-diglycidyl methacrylate (bis GMA) polymerizable through the action of peroxide systems such as benzoyl peroxide mixed with amines, (Vuillemin et al. (1987) Arch. Otolygol. Head Neck Surg. 113: 836-840). Two components, resin composites containing both salicylates and acrylates, cured through a calcium hydroxide cement reaction are described in U.S. Pat. No. 4,886,843, while U.S. Pat. Nos. 5,145,520 and 5,238,491 disclose fillers and cements. The foregoing materials can be fabricated so as to incorporate NELL-1 proteins.

In addition, graft materials that include bone morphogenic proteins are known. Thus, for example, U.S. Pat. No. 4,394,370 describes complexes of reconstituted collagen and demineralized bone particles or reconstituted collagen and a solubilized bone morphogenetic protein fabricated in a sponge suitable for in vivo implantation in osseous defects are disclosed. Similarly U.S. Pat. No. 5,824,084 describes substrates made from a biocompatible, implantable graft material, preferably having a charged surface. Examples of biocompatible, implantable graft materials include synthetic ceramics comprising calcium phosphate, some polymers, demineralized bone matrix, or mineralized bone matrix. These materials can additionally contain cell adhesion molecules bound to the surface of the substrate. The term "cell adhesion molecules" refers collectively to laminins, fibronectin, vitronectin, vascular cell adhesion molecules (V-CAM) and intercellular adhesion molecules (I-CAM) and collagen. Particularly suitable graft materials include, for example, isolated mineralized cancellous bone sections, powders or granules of mineralized bone, demineralized cancellous bone sections, powders or granules of demineralized bone, guanidine-HCl extracted demineralized bone matrix, sintered cortical or cancellous bone, coralline hydroxyapatite sold by Interpore under the trade name Interpore 500, and granular ceramics such as that incorporated into the bone graft substitute Collagraft sold by Zimmer, or filamentous sponges such as those made from collagen by Orquest. NELL-1 proteins can be incorporated into any of these graft materials or substituted in place of the bone morphogenic protein.

VII. Kits.

In still another embodiment, this invention provides kits for practice of the assays or use of the compositions described herein. In one preferred embodiment, the kits comprise one or more containers containing antibodies and/or nucleic acid probes and/or substrates suitable for detection of NELL-1 gene expression and/or activity levels. The kits can optionally include any reagents and/or apparatus to facilitate practice of the assays described herein. Such reagents include, but are not limited to buffers, labels, labeled antibodies, labeled nucleic acids, filter sets for visualization of fluorescent labels, blotting membranes, and the like.

In another embodiment, the kits can comprise a container containing a NELL-1 protein, a related agent described above, or a vector encoding a NELL-1 protein and/or a cell comprising a vector encoding a NELL-1 protein.

In addition, the kits can include instructional materials containing directions (i.e., protocols) for the practice of the assay methods of this invention or the administration of the compositions described here along with counter indications. While the instructional materials typically comprise written or printed materials they are not limited to such. Any medium capable of storing such instructions and communicating them to an end user is contemplated by this invention. Such media include, but are not limited to electronic storage media (e.g. magnetic discs, tapes, cartridges, chips), optical media (e.g. CD ROM), and the like. Such media can include addresses to internet sites that provide such instructional materials.

3) NELL-1 for Osteoporosis

In some embodiments, the NELL-1 protein described herein can be used to treat, prevent, or ameliorate osteoporosis. In this embodiment, the NELL-1 peptide can be administered to a site of osteoporosis. Subsequently, a physical force such as a vibration or ultrasound can be applied to the site of administration to disperse the NELL-1 peptide. In some embodiments, the NELL-1 peptide can be administered to the site of osteoporosis by the acts of (a) making an incision in a tissue (bone) and (b) delivering to the tissue through the incision the NELL-1 peptide. In some embodiments, the Nell-1 peptide can be in a pharmaceutically acceptable carrier for sustained delivery.

4) NELL-1 for Cartilage Regeneration

In some embodiments, the NELL-1 protein described herein can be used to treat, prevent, or ameliorate cartilage degeneration. In one embodiment, the NELL-1 peptide can be administered to a site of fibrocartilage disease such as spinal disc disease with or without a pharmaceutically acceptable carrier, with or without other devices (e.g., disc nucleus replacement device, allograft device, or cells) or biological factors (e.g., LIM-1 protein). In another embodiment, the NELL-1 peptide can be administered to a site of fibrocartilage disease such as meniscus, with or without a pharmaceutically acceptable carrier, with or without other devices (e.g., meniscus allograft or meniscus scaffold or prosthesis, or cells) or biological factors. In another embodiment, the NELL-1 peptide can be administered to a site of hyaline cartilage disease such as knee articular cartilage, with or without a pharmaceutically acceptable carrier, with or without other devices (e.g., cartilage allograft or cartilage scaffold or prosthesis) or biological factors. In another embodiment, the NELL-1 peptide can be administered to another site of hyaline cartilage disease such as tracheal cartilage (e.g., tracheomalacia), with or without a pharmaceutically acceptable carrier, with or without other devices (e.g., cartilage allograft or cartilage scaffold or prosthesis) or biological factors.

In other embodiments, the NELL-1 peptide can be administered to a site of elastic cartilage disease such as auricular or epiglottis with or without a pharmaceutically acceptable carrier, with or without other devices (e.g., cells) or biological factors.

Administration of Composition

A composition described herein can be formulated into formulations suitable for any suitable mode of administration/delivery to a mammalian subject (e.g., a human being). An ordinary artisan with the teachings above can formulate the composition described here into any desirable formulation by using, e.g., an appropriate carrier with an appropriate amount of a NELL peptide or a related agent defined above.

Some examples of delivering the composition can be, e.g., percutaneous injection through intact skin to various sites, or direct injection through nonintact skin (e.g., surgically opened sites or trauma sites). In some embodiments, the delivery can be surgical implantation of a composition described herein. In some embodiments, the delivery can be one of extravascular delivery, injection or catheter based injections; intravascular delivery, injection or catheter based injections; intravenous delivery, injection or catheter based injections; intraarterial delivery, injection or catheter based injections; intrathecal delivery, injection or catheter based injections; intraosseous delivery, injection or catheter based injections; intracartilaginous delivery, injection or catheter based injections; or intravesical delivery, injection or catheter based injections.

In some embodiments, a delivery of composition described herein to a mammalian subject can be delivery via mechanical pumps with percutaneous or implantable catheters.

In some embodiments, a delivery of composition described herein to a mammalian subject can be catheter based delivery to any area/organ in the body.

In some embodiments, a delivery of composition described herein to a mammalian subject can be delivery via expanded dispersion through various devices promoting increased tissue penetration or wider tissue distribution (e.g., ultrasound, iontophoresis, heat, pressure, etc.)

EXAMPLES

The following example illustrates, but not to limit the claimed invention.

Example 1

NELL-1 Enhances Mineralization in Fetal Calvarial Osteoblastic Cells

The nucleotide sequence of the full length cDNA of the NELL-1 gene described herein has approximately 61% homology to the chicken Ne1 gene, and therefore, was named human NELL-1 (Watanabe et al. (1996) Genomics. 38(3), 273-276). NELL-1 proteins contain a signal peptide, a $NH_2$-terminal thrombospondin (TSP)-like module (Francois and Bier (1995) Cell. 80(1):19-20), five von Willebrand factor C domains, and six EGF-like domains.

The human NELL-1 gene expressions were primarily localized in the mesenchymal and osteoblast cells at the osteogenic front, along the parasutural bone margins, and within the condensing mesenchymal cells of newly formed bone. A human multiple-organ tissue mRNA blot showed that human NELL-1 gene was specifically expressed in fetal brain but not in fetal lung, kidney or liver. We also demonstrated that NELL-1 gene was expressed in rat calvarial osteoprogenitor cells but was largely absent in rat tibia, stromal cell, and fibroblast cell culture. Our data suggest that the NELL-1 gene is preferentially expressed in cranial intramembranous bone and neural tissue (neural crest origin).

FIG. 1A illustrates over-expression of NELL-1 in E-14 rat calvarial primary cell cultures using adenoviruses with beta-galactosidase as control. FIG. 1B shows a plot of mineralization as a function of time post treatment with NELL-1 and beta-glactosidase respectively. Experiments were performed in triplicate. Student's T test was performed. Mineralization with NELL-1 was statistically higher than mineralization with .beta.-Galactosidase control, *P<0.001.

A) MATERIALS AND METHODS

Whole mouse embryo RNA analysis from the fetal gestation day 7, 11, 14, 17, was performed. Adenoviruses (AD5 with an E1-A knock-out and MCV promoter) carrying NELL-1 cDNA were constructed and infected into rat fetal calvarial primary cell cultures and MC3T3 cell lines. Viruses were constructed according the following protocol: the 293 cells were co-transfected with 10 mg each of pJM17 (containing defective adenovirus genome) and pAC-CMV-based plasmid (containing sense or antisense rat NELL-1 using $CaPO_4$) to produce recombinant adenovirus vectors expressing rat NELL-1 in 10-14 days. Viruses were plaque-purified and Southern blots were performed to assure the incorporation of the NELL-1 gene. Adenoviruses containing the .beta.-Galactosidase gene were used as a control and examined for the efficacy of infection with different cell types. Approximately 80-90% infection efficiency was observed in both MC3T3 and NIH3T3 cells.

Von Kossa staining was performed on 14, 17, 21 day post-infections. Area of mineralization was quantified by ImagePro system. Statistical analysis was performed by two-tailed Student's t test. A statistical P value of *p<0.01 was considered significant. RNA from cells over-expressing NELL-1 was extracted and mouse cDNA array analysis was performed. Hybridization signals were quantitated by phosphoimager.

B) RESULTS

NELL-1 mRNA was faintly expressed from day 14 of gestation with mild increase over the gestation period. Day 14 gestation is the time point when fetal calvaria starts to mineralize. Both primary rat fetal calvarial cell cultures and MC3T3 cell cultures over-expressing NELL-1 showed an increase in mineralization over the .beta.-Galactosidase control. Over-expression of NELL-1 enhanced mineralization in calvarial osteogenic primary cell cultures by approximately 30 folds on day 17 post-infection compared to the control. These results were based on Von Kossa staining and quantitated by ImagePro software. This relative increase decreased to 2 fold by day 21 post infection. Mouse cDNA array results from NELL-1 infected MC3T3 cells showed 20% down regulation in BMP-7 gene expression and a three fold up regulation of the Split Hand and Foot gene compared to the control. These two genes are closed related to bone formation and craniofacial development.

C) DISCUSSIONS AND CONCLUSIONS

In this study, we clearly confirmed that NELL-1 is closely associated with bone formation and it enhanced mineralization of the calvarial osteoblast-like cells. Some of the down stream effectors identified clearly play important roles in bone formation and embryological development. Premature cranial suture closure, as seen in CS, can be due to overproduction of cranial bone, and therefore, possibly be associated with the over-expression of the NELL-1 molecule. These results and the preliminary protein function analysis results of the NELL-1 classify this protein as a biologically relevant molecule. As a possible role of NELL-1, these proteins can act as a modulator, interacting with other growth factors. Recently, TSP-1 was shown to be a major activator of TGF. beta.-1 (Francois and Bier (1995) Cell. 80(1):19-20). TGF. beta.-1 is secreted by most cells in an inactive form that is unable to interact with cellular receptors. The activity of TGF.beta.-1 is initially masked by its noncovalent association with a dimer of its $NH_2$-terminal propeptide, called latency-associated protein (LAP). In activating TGF.beta.-1 extracellularly, TSP-1 interacts with the $NH_2$-terminal region of LAP, forming a trimolecular complex. Within the complex, a conformational change takes place that makes TGF.beta.-1 accessible to the receptor. Molecules with high homology like chordin, which possess four vWF C domains (presumably homotrimer), can be secreted during gastrulation and plays a pivotal role in the Xenopus dorsoventral patterning (Crawford et al. (1998) Cell. 93(7): 1159-1170). Recently, chordin was revealed to directly bind to ventral BMP-4 (bone morphogenetic proteins 4, one of the TGFβ superfamily) and neutralize the BMP-4 activity (Piccolo et al. (1996) Cell, 86(4):589-598). These results suggest that NELL-1 protein can execute their unidentified functions extracellularly by interacting with some of the TGFβ superfamily members. Since TGFβ-1 is known as a regulator of osteogenesis, NELL-1 protein's effect in enhancing mineralization can be related to its interaction with the TGFβ superfamily.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

I claim:

1. A method of increasing bone mineralization, the method comprising increasing the concentration of a NELL-1 gene product in an osteogenic cell by administering a NELL-1 gene product in an effective amount to the osteogenic cell;
   wherein the NELL-1 gene product is a NELL-1 protein or an osteogenic fragment thereof,
   wherein the NELL-1 protein comprises the amino acid sequence of SEQ ID NO: 1 or 8.

2. The method of claim 1, wherein the osteogenic cell is selected from the group consisting of a mature osteoblast, an osteoblast, a mesenchymal cell, a fibroblast cell, a fetal embryonic cell, a stem cell, a bone marrow cell, a dura cell, a chrondrocyte, and a chondroblast.

3. A method of facilitating the repair of bone fractures, the method comprising increasing the concentration of a NELL-1 gene product at or near the fracture site by administering a composition comprising a NELL-1 gene product at or near the bone fracture site,
   wherein the NELL-1 gene product is a NELL-1 protein or an osteogenic fragment thereof,
   wherein the NELL-1 protein comprises the amino acid sequence of SEQ. ID. NO: 1 or 8.

4. A method of facilitating the repair of a bone fracture, the method comprising administering to the bone fracture site a composition comprising a NELL-1 protein,
   wherein the NELL-1 protein comprises the amino acid sequence of SEQ ID NO: 1 or 8.

5. The method of claim 4, wherein the composition further comprises a pharmaceutically acceptable carrier.

6. The method of claim 5, wherein the pharmaceutically acceptable carrier comprises collagen.

7. A method of treating, preventing or ameliorating osteoporosis by administering to a bone tissue at a pre-selected site an effective amount of a NELL-1 protein or an osteogenic fragment thereof, wherein the NELL-1 protein comprises the sequence of SEQ ID NO: 1 or 8.

8. The method of claim 7, further comprising applying to the pre-selected site a physical force to disperse the NELL-1 protein.

9. The method of claim 8, wherein the administering step comprises:
   making an incision in the bone tissue at the pre-selected site, and
   delivering to the bone tissue at the pre-selected site via the incision.

10. The method of claim 8, wherein the physical force is ultrasound.

11. The method of claim 7, wherein the NELL-1 protein is formulated into a formulation suitable for a mode of delivery selected from percutaneous injection through intact skin to a site, direct injection through a surgically opened site or a trauma site, surgical implantation, extravascular delivery, extravascular injection, extravascular catheter based injection, intravascular delivery, intravascular injection, intravascular catheter based injections, intravenous delivery, intravenous injection, intravenous catheter based injections, intraarterial delivery, intraarterial injection, intraarterial catheter based injections, intrathecal delivery, intrathecal injection, intrathecal catheter based injections, intraosseous delivery, intraosseous injection, catheter based injections, intracartilaginous delivery, intracartilaginous injection, intracartilaginous catheter based injections, intravesical delivery, intravesical injection, intravesical catheter based injection, delivery via a mechanical pump with a percutaneous or implantable catheter, catheter based delivery to an area or organ in the body, or delivery via expanded dispersion through a device that increases tissue penetration or wider tissue distribution.

12. The method of claim 11, wherein the device provides ultrasound, iontophoresis, heat or pressure.